US011103590B2

(12) United States Patent
Ohno

(10) Patent No.: US 11,103,590 B2
(45) Date of Patent: Aug. 31, 2021

(54) IMMUNOSTIMULANT

(71) Applicant: CELL-MEDICINE, INC., Ibaraki (JP)

(72) Inventor: Tadao Ohno, Ibaraki (JP)

(73) Assignee: CELL-MEDICINE, INC., Ibaraki (JP)

( * ) Notice: Subject to any disclaimer, the term of this patent is extended or adjusted under 35 U.S.C. 154(b) by 0 days.

(21) Appl. No.: 16/329,919

(22) PCT Filed: Sep. 5, 2017

(86) PCT No.: PCT/JP2017/031879
§ 371 (c)(1),
(2) Date: Mar. 1, 2019

(87) PCT Pub. No.: WO2018/047797
PCT Pub. Date: Mar. 15, 2018

(65) Prior Publication Data
US 2019/0192676 A1  Jun. 27, 2019

(30) Foreign Application Priority Data

Sep. 6, 2016 (JP) .............................. JP2016-173357

(51) Int. Cl.
| | | |
|---|---|---|
| *A61K 47/62* | (2017.01) | |
| *A61K 38/42* | (2006.01) | |
| *A61K 39/395* | (2006.01) | |
| *A61P 35/00* | (2006.01) | |
| *A61P 35/04* | (2006.01) | |
| *A61K 39/00* | (2006.01) | |
| *A61K 39/39* | (2006.01) | |
| *A61K 38/44* | (2006.01) | |
| *A61K 47/64* | (2017.01) | |
| *A61K 38/19* | (2006.01) | |
| *A61K 38/21* | (2006.01) | |
| *A61K 38/20* | (2006.01) | |
| *A61K 39/04* | (2006.01) | |
| *A61P 37/04* | (2006.01) | |
| *A61K 31/713* | (2006.01) | |
| *A61K 38/16* | (2006.01) | |

(52) U.S. Cl.
CPC ............ *A61K 47/62* (2017.08); *A61K 31/713* (2013.01); *A61K 38/164* (2013.01); *A61K 38/19* (2013.01); *A61K 38/20* (2013.01); *A61K 38/21* (2013.01); *A61K 38/42* (2013.01); *A61K 38/44* (2013.01); *A61K 39/00* (2013.01); *A61K 39/0011* (2013.01); *A61K 39/04* (2013.01); *A61K 39/39* (2013.01); *A61K 39/395* (2013.01); *A61K 47/64* (2017.08); *A61P 35/00* (2018.01); *A61P 35/04* (2018.01); *A61P 37/04* (2018.01); *A61K 2039/55516* (2013.01)

(58) Field of Classification Search
None
See application file for complete search history.

(56) References Cited

U.S. PATENT DOCUMENTS

| | | | |
|---|---|---|---|
| 7,247,310 | B1 | 7/2007 | Ohno et al. |
| 7,722,857 | B2 * | 5/2010 | Ohno .................... A61K 39/39 |
| | | | 424/1.61 |
| 10,441,539 | B2 * | 10/2019 | Ragg ......................... A61P 9/14 |
| 2006/0008478 | A1 | 1/2006 | Ohno et al. |
| 2009/0274763 | A1 * | 11/2009 | Ohno ..................... A61K 39/39 |
| | | | 424/489 |
| 2019/0192676 | A1 * | 6/2019 | Ohno ..................... A61K 39/04 |
| 2020/0010539 | A1 * | 1/2020 | Bieck .................. C07K 14/4725 |
| 2020/0397895 | A1 * | 12/2020 | Levy .................... A61K 39/3955 |

FOREIGN PATENT DOCUMENTS

| | | | |
|---|---|---|---|
| EP | 1683517 | 7/2006 | |
| EP | 1683517 A1 * | 7/2006 | ............. A61K 9/167 |
| JP | 2001-010961 | 1/2001 | |
| JP | 2001-058955 | 3/2001 | |
| JP | 2003-306444 | 10/2003 | |
| JP | 3492671 | 2/2004 | |
| JP | 4176021 | 11/2008 | |
| JP | 4238279 | 3/2009 | |
| JP | 4569946 | 10/2010 | |
| JP | 4688254 | 5/2011 | |
| JP | 5579586 | 8/2014 | |
| WO | WO-2018047797 A1 * | 3/2018 | ............. A61K 38/20 |

OTHER PUBLICATIONS

Gillespie et al, Vaccine 34 (2016) 2992-2995. available online Mar. 11, 2016 (Year: 2016).*
M.R. Alderson / Vaccine 34 (2016) 2959-2961 (Year: 2016).*
Beaumier et al, Vaccine 34 (2016) 2996-3000 (Year: 2016).*
Birkett, Vaccine 34 (2016) 2915-2920 (Year: 2016).*
NCI Fact Sheet in Cancer Vaccine , 2011, 9 pages (Year: 2011).*
Rubtsova et al., "Chemiluminescent biosensors based on porous supports with immobilized peroxide," *Biosensors & Bioelectronics*, vol. 13, No. 1, pp. 75-85 (1998).
Bodet et al., "Hemoglobin and LPS act in synergy to amplify the inflammatory response", *J. Dent. Res.*, vol. 86, No. 9, pp. 878-882 (2007).
Zhao et al., "Bovin serum albumin promotes IL-1beta secretion by N9 microglial cells", Neurol Sci, vol. 30, 2009, pp. 379-383.
Chu et al., "Neutrophil-mediated delivery of therapeutic nanoparticls across blood vessel infection", ACS Nano, vol. 9, No. 12, 2015, p. 11800-11811.

(Continued)

*Primary Examiner* — Nita M. Minnifield
(74) *Attorney, Agent, or Firm* — Greenblum & Bernstein, P.L.C.

(57) ABSTRACT

A complex comprising a carrier containing a plasma-derived protein or serum-derived protein solidified by denaturation coagulation, and a protein having a peroxidase-like activity and carried by the carrier, which has such high effectiveness that it can strongly stimulate an antigen-presenting cell, and can be used as a highly safe immunostimulant with reduced toxicity to living bodies.

15 Claims, 7 Drawing Sheets

(56) References Cited

OTHER PUBLICATIONS

"Medical Note of EARL", http://drmagician.exblog.jp/16073684, pp. 1-4 with English Translation.
Sakai Harumi, Clinical Virology (Rinsho to Virus), 41(5): 1-9 (2013) with English Tanslation.
Stills HF, Jr., "Adjuvants and antibody production: Dispelling the myths associated with Freund's complete and other adjuvants", ILAR Journal, 46:280-293, (2005).
Kuroda F. et al., "Particulate adjuvant and innate immunity: Past achievements, present findings, and future prospects," *Intern. Rev. Immunol.*, 32:209-220, (2013).
Disis ML et al., "Granulocyte-macrophage colony-stimulating factor: an effective adjuvant for protein and peptide-based vaccines", *Blood*, 88:202-210, (1996).
Yutani S. et al., "Phase II study of personalized peptide vaccination with both a hepatitis C virus-derived peptide and peptides from tumor-associated antigens for the treatment of HCV-positive advanced hepatocellular carcinoma patients", J. Immunol. Res., Article ID 473909, 2015, http://www.hindawi.com/journals/jir/2015/473909/.
Kuang M. et al., "Phase II randomized trial of autologous formalin-fixed tumor vaccine for postsurgical recurrence of hepatocellular carcinoma", *Clin. Cancer Res.*, 10:1574-1579, (2004).
Hashimoto N. et al., "Wilms tumor 1 peptide vaccination combined with temozolomide against newly diagnosed glioblastoma: safety and impact on immunological response", Cancer Immunol. Immunother., 64:707-16, (2015).
Kawashima I. et al., "Suppression of postsurgical recurrence of hepatocellular carcinoma treated with autologous formalin-fixed tumor vaccine, with special reference to glypican-3", Clinical Case Reports, 3:444-447, (2015).
Muragaki Y. et al., "Phase I /IIa Trial of Autologous Formalin-fixed Tumor Vaccine Concomitant with Fractionated Radiotherapy for Initially-Diagnosed Glioblastoma", J. Neurosurg., 115:248-255, (2011).
Ishikawa E. et al., "Phase I/IIa trial of fractionated radiotherapy, temozolomide, and autologous formalin-fixed tumor vaccine for newly diagnosed glioblastoma", J. Neurosurg., 121:543-553, (2014).
Kunins H. V. et al., "Validity of a self-reported history of a positive tuberculin skin test—A prospective study of drug users", J. Gen. Intern. Med., 19:1039-1044, (2004).
"Ministry of Health, Labor and Welfare homepage, Introduction of allergy", Chapter 1, http://www.mhlw.go.jp/new-info/kobetu/kenkou/ryumachi/dl/jouhou01-17.pdf, ., p. 8, para. 4. With English excerpt.
Kurosaka K. et al., "Production of proinflammatory cytokines by phorbol myristate acetate-treated THP-1 cells and monocyte-derived macrophages after phagocytosis of apoptotic CTLL-2 cells", J. Immunol., 161:6245-6249, 1998.
Landi S. et al., "Evaluation of various substances to prevent adsorption of tuberculin purified protein derivative (PPD) to glass surfaces", Bull. Org. mond. Sant. Bull. Wld. Hlth. Org., 43:91-106, 1970.
Hu P.Q. et al., "*Escherichia coli* expressing recombinant antigen and listeriolysin O stimulate class I-restricted CD8+ T cells following uptake by human APC", J. Immunol., 172:1595-1601, 2004.
Brett S.J. et al., "Comparison of antigen presentation of influenza A nucleoprotein expressed in attenuated AroA-*Salmonella typhimurium* with that of live virus", J. Immunol., 150:2869-2884, 1993.
Oliveira M.M. et al., "*Mycobacterium bovis* BCG but not *Mycobacterium leprae* induces TNF-alpha secretion in human monocytic THP-1 cells", Mem. Inst. Oswaldo. Cruz., 96(7):973-978, 2001.
Gordon S., "The macrophage: past, present and future", Eur. J. Immunol., 37: Suppl 1:S9-17, 2007.
Cho Y.S. et al., "Deciphering the proteome of the in vivo diagnostic reagent "purified protein derivative" from *Mycobacterium tuberculosis*, Proteomics", 12 (7):979-991, 2012, doi: 10.1002-/pmic.201100544.
Chang Z.L., "Recent development of the mononuclear phagocyte system: in memory of Metchnikoff and Ehrlich on the 100th Anniversary of the 1908 Nobel Prize in Physiology or Medicine", Biol. Cell., 101 (12):709-721, 2009.
Najjam S. et al., "Further characterization of the binding of human recombinant interleukin 2 to heparin and identification of putative binding sites", Glycobiology, 8:509-516, 1998.
"DAKO Educational IHC Guidebook, Immunohistochemical Staining Methods", Sixth Edition, Chapter 15, ed. Tayor CR and Rudbeck L, 2013, http://www.dako.com.
Ishikawa E. et al., "Clinical trial of autologous formalin-fixed tumor vaccine for glioblastoma multiforme patients", Cancer Sci, 98:1226-1233,(2007).
International Search Report in International Patent Application No. PCT/JP2017/031879, dated Oct. 24, 2017.
International Preliminary Report on Patentability issued in PCT/JP2017/031879, dated Mar. 12, 2019, along with an English-language translation.
Extended European Search Report, European Patent Office, corresponding European patent application No. 17848737.7, dated Apr. 20, 2020.
Ishikawa et al., "Intratumoral injection of IL-2-activated NK cells enhances the antitumor effect of intradermally injected paraformaldehyde-fixed tumor vaccine in a rat intracranial brain tumor model" Cancer Science, Jan. 2004, vol. 95, No. 1, pp. 98-103, XP055173453.
Ishii K, Research and development, production, and distribution division meeting, Data 1, Jan. 30, 2015.
Guld J, Standardization and Stability of Purified Tuberculin, American Review of Respiratory Disease, The American Review of Respiratory Diseases, 80(2), pp. 255-256, Aug. 1959.

* cited by examiner

IMMUNOSTIMULANT

TECHNICAL FIELD

The present invention relates to an immunostimulant. More specifically, the present invention relates to an immunostimulant containing a plasma-derived protein or serum-derived protein solidified by denaturation coagulation as a carrier.

BACKGROUND ART

It is known that immunity is broadly classified into two kinds, i.e., innate immunity and acquired immunity. Substances that trigger inflammatory reactions in living bodies mainly stimulate the innate immunity, and causes inflammatory reactions in several minutes to several days. Then, the acquired immunity is induced, and there occurs reactions specific to a substance that acts as an antigen. These reactions include humoral immunoreactions (antibody production) mainly induced by B cells, and cell-mediated immunoreactions (removal of abnormal cells via the cytotoxic reaction) induced by T cells. Vaccines are used for administering antigens to a living body to stimulate immunity and thereby prevent (or sometimes treat) a disease such as infectious diseases. When immunostimulating ability of an antigen expected to induce immunoreactions is weak (i.e., low antigenicity), an immunoadjuvant can be added for assisting the immune stimulation to enhance immunoreactions against the antigen.

Immunoadjuvants are integrated with an antigen by a certain means such as adsorbing, covering, or confining an antigen, or bonding an antigen with a covalent bond, and devised so that the antigen should not easily spread and disappear in the inside of a body. These devised processes as described above correspond to a process in which the antigen should be once incorporated into an antigen-presenting cell (dendritic cell, macrophage, monocyte, and B cell are known), and processed within the cell, irrespective of which one of the humoral immunoreaction and cell-mediated immunoreaction the antigen induces. The processed antigen is carried by the major histocompatibility complex (henceforth abbreviated as "MHC"), presented on the surface of an antigen-presenting cell, and recognized by a helper T cell, which leads to induction of humoral immunoreactions or cell-mediated immunoreactions. Therefore, for the expected induction of immunoreactions against the antigen, immunoadjuvants are generally administered from the outside of the body together with the antigen, or topically administered to a site in the body where the antigen exists. A group of substances expected to exhibit an action of stimulating the general immunoreaction system without using any antigen (and accordingly, it is not necessarily expected to induce an immunoreaction specific to the antigen) are usually classified as "biological response modifiers (BRMs)", and prominent examples thereof include Krestin, Lentinan, and Maruyama vaccine.

Among antigens incorporated into an antigen-presenting cell and processed therein, those presented on the class II molecules of MHCs mainly induce antigen-specific antibody production by mature B cells via activation of Th2 type helper T cells. The produced antibodies play the leading role of the humoral immunoreactions. Further, those antigens presented on the class I molecules of MHCs mainly proliferate and activate antigen-specific cytotoxic T cells (CTLs) via activation of Th1 type helper T cells. That is, the Th1 type helper T cells and CTLs play the leading roles of the cell-mediated immunoreactions. It is understood that, in both of the humoral immunoreactions and cell-mediated immunoreactions, an immunoadjuvant contained in a vaccine generally enhances acquired immunity via innate immunity (Non-patent document 1). All the descriptions in the patent documents and non-patent documents cited in this specification are incorporated by reference into the disclosure of this specification.

Since there was suggested the concept of use of activation of the immune system in the body not only as precautions against infectious diseases by external organisms, but also for treatment of tumors (including carcinomas) generated in the inside of the body of the same individual (Coley, 1891), over 100 years has already passed. However, it is hard to say that tumor vaccines based on the same scheme as that used for infectious disease vaccines (that is, combination of an antigen and an immunoadjuvant) achieve satisfactory results in oncotherapies even today.

The immunoreaction system includes immune checkpoints that suspend activation of lymphocytes, and development of a method for enhancing immunoreactions by overcoming this wall constitutes a research topic. As immunotherapy of tumors, there is known use of an anti-PD-1 antibody, nivolumab, which was approved in this country in July, 2014 for the first time in the world. This antibody drug has an action of activating immunoreactions by an action of inhibiting immune checkpoints, and is supposed to be highly effective for melanoma, lung cancer, renal carcinoma, and the like. However, types of cancer on which it is effective are limited only to some kinds of cancers, and it is effective in only about 30% of cases. Since there are intractable tumors for which even prophylactic treatment of postoperative recurrence is very difficult even with a combination of all of the conventional surgical operations, radiotherapies, and chemotherapies, like, for example, glioblastoma among the brain tumors, social needs expecting development of other oncotherapies not based on the immune checkpoint inhibitors, but based on other effective enhancement of immunoreactions are extremely high.

As candidates of immunoadjuvants, there are substances that bind with pattern-recognition receptors that induce innate immunity. Examples thereof include exogenous Toll-like receptor agonists, NOD-like receptor agonists, and RIG-like receptor agonists, which are known as pathogen-associated molecular patterns, as well as endogenous alarmins. There are also substances that bind with receptor of advanced glycation endproduct, cytokines, chemokines, and the like, and there are a huge number of types thereof (Non-patent document 2).

Among these immunostimulating substances, bacteria-derived lipoproteins, lipopeptides, lipoteichoic acid, Mycobacteria-derived lipoglycans, mycoplasma-derived lipoproteins, yeast-derived zymosan, porin, viral dsRNA, lipopolysaccharides of gram-negative bacilli, lipid A, monophosphoryl lipid A, lipopolysaccharides, heat shock proteins, flagellin, viral ssRNA, imidazoquinoline, bacterial DNA, CpG DNA, hemozoin, uropathogenic bacteria, profilin, and profilin-like proteins of protozoa, as well as saponin, bacterial toxins, and the like are relatively frequently used as immunoadjuvants (Non-patent document 1). Although potency of their actions varies widely, all of these substances are inflammation inducers, and induce intracellular signals, which lead to production of cytokines.

As delivery systems of the inflammation inducers, there are known aluminum salts, oil or fat/water emulsion (containing surfactant as emulsifier), liposome, virosome, biologically degradable artificial polymer microglobules, immune stimulating complex (ISCOM), squalene, alpha-tocopherol, and mucosal delivery system (Non-patent document 1). Besides these substances, there are also known calcium phosphate (Patent document 1), and silica (Non-patent documents 3 and 4). Among cytokines, as those showing high immunoreaction-stimulating ability, granulocyte-macrophage colony-stimulating factor (GM-CSF) is known (Non-patent document 5), and in addition, there are interleukin-12 (Non-patent document 6), and the like.

Known as the most potent immunoadjuvant is Freund's complete adjuvant (FCA, mixture of liquid paraffin, surfactant, and tubercular dead cells) (Non-patent document 3). However, since it shows strong toxicity due to induction of intense inflammation, it is used only for the experimental purpose in these days. In the field of oncotherapy, clinical use of Freund's incomplete adjuvant (IFA) not containing tubercular dead cells (for example, Montanide ISA-51) as an immunoadjuvant of cancer peptide vaccine is attempted (Non-patent documents 7 and 8). However, it is known that even IFA induces severe inflammatory reactions, and when it is subcutaneously injected, rubor and swelling remain at the injection site over such a long period of time as several months or longer, occasionally one year or longer.

The most widely used clinical immunoadjuvant in a vaccine composition for prevention of infectious diseases is aluminum salt and aluminum hydroxide. However, although they show superior ability to enhance the humoral immunoreactions, they suffer from a problem of low cell-mediated immunoreaction-inducing ability (Non-patent documents 4 and 6).

It is widely known that, in a treatment or prophylactic treatment of recurrence of tumor, even if not only innate immunity, but also acquired immunity can be stimulated, induction of humoral immunoreactions alone is not sufficient, and activation of helper T cells (especially Th1 type helper T cells) and CTL by induction of cell-mediated immunoreactions, and tumor cell-killing action of CTL are important. For this reason, there are desired an immunoadjuvant and immunostimulant that have characteristics different from those of aluminum salt or aluminum hydroxide, and can specifically activate cell-mediated immunoreactions. However, among the various kinds of known immunoadjuvants, those having high cell-mediated immunoreaction-inducing ability such as FCA or IFA mentioned above tend to also show strong toxicity caused by inflammation induction, and have a problem of difficulty in clinical application thereof. It cannot be said that useful and highly safe immunoadjuvants showing superior cell-mediated immunoreaction-enhancing ability and low toxicity have been sufficiently developed.

The inventors of the present invention prepared an autologous cancer vaccine using precipitates of albumin-heparin coacervate bound with GM-CSF, interleukin-2 (IL-2), and/or purified tuberculin as an immunoadjuvant, and an operatively resected formalin-fixed autologous liver cancer tissue fragment as an antigen for inducing cell-mediated immunoreactions. This vaccine is highly safe, that is, when it was used for 18 liver cancer patients, it showed adverse events only at a level of the grade 1 to 2 according to National Cancer Institute—Common Toxicity Criteria v. 2.0, 1999, which means adverse events with self-healing, and no patient showed critical adverse event of the grade 3 to 4. A postoperative recurrence-preventing effect thereof for liver cancer was observed, and effectiveness thereof was also confirmed (Non-patent document 9, and Patent document 2).

An operatively resected formalin-fixed liver cancer tissue fragment as an antigen, which adsorbed a BCG bacteria extract (BCGext) as an immunoadjuvant, and albumin-heparin coacervate precipitates containing purified tuberculin fixed by crosslinking reaction, to which dissolved purified tuberculin is further added, can be used as autologous liver cancer vaccines, and it was observed in liver cancer cases that CTL against the liver cancer-specific antigen molecule, glypican 3, was induced by these vaccines (Non-patent document 10).

Formalin-fixed autologous glioblastoma tissue fragments as an antigen containing BCGext as an immunoadjuvant (Patent document 3), and albumin-heparin coacervate precipitates containing purified tuberculin fixed by crosslinking reaction (Patent document 4), to which dissolved purified tuberculin is further added and mixed, can be used as an autologous brain tumor vaccine. There was observed prolongation of overall postoperative survival time provided by this vaccine was observed in glioblastoma patients in comparison with a historical control group of which data were historical control data mentioned in literatures (Non-patent documents 11, 12, and 13). High safety was demonstrated also in these clinical trials, where no patient showed critical adverse event of the grade 3 to 4, either.

The aforementioned autologous brain tumor vaccine utilizes a formalin-fixed autologous brain tumor tissue as a carrier of the immunostimulating substance. However, a sufficient amount of resected tumor tissue may not be available in some patients. Therefore, a substitute for the formalin-fixed tumor tissue is required, and has been actively searched for. In the process of the development thereof, there have been proposed soluble serum proteins fixed and carried on an insoluble substance serving as a base, such as albumin carried by calcium phosphate precipitates, which are inorganic solid (Patent document 1), and albumin made into albumin-heparin coacervate precipitates (Patent documents 4 and 5). In these forms, the albumin molecules themselves are in a state that they are not denatured, but maintain the original molecular form thereof. In the former, albumin molecules are rolled in calcium phosphate precipitates, and in the latter, they are crosslinked in a state of coacervate with an intermolecular crosslinking agent for proteins. However, it has not been known so far that albumin molecules themselves preliminarily coagulated by denaturation and solidified by crosslinking with an intermolecular crosslinking agent for proteins act as an effective carrier of an antigen or an immunostimulating substance.

Insoluble microparticles prepared from a solidified material selected from the group consisting of tissue, cells, and ingredients thereof of an animal or human can also be used (Patent document 6). However, Patent document 6 mentioned above does not disclose that proteins extracellularly secreted and dissolved in the plasma can be used instead of the tissue, cells, or ingredients thereof, and it also fails to suggest nor teach such a technical concept. There cannot be found any reference that suggests or teaches use of proteins dissolved in the plasma (or serum) themselves preliminarily coagulated by denaturation at a molecular level and made into an insoluble solid by a treatment with an intermolecular crosslinking agent for proteins as a major carrier or composition of an immunostimulating substance (as a delivery system of inflammation inducers).

As is well known, if a tissue, cell of an animal, or a material comprising ingredients thereof is administered to a xenogenic animal, rejection reaction arises. Since it has been presumed that the rejection is caused even when such a material is processed and solidified, such a material has not been widely used in human clinical cases even if the material can be easily obtained, except for some materials such as collagen that shows extremely low antigenicity. Although human plasma-derived proteins originally dissolved in the blood can be obtained in a comparatively large amount, it has not investigated in detail so far whether rejection is induced when such protein molecules are processed by denaturation and administered to the same species, human. Because of such a background, there is no reference that suggests or teaches the technical concept of processing plasma-derived proteins to make them insoluble, and using them as a carrier of an antigen or an immunostimulating substance, and there is no reference that suggests or teaches that a carrier prepared in such a manner as described above scarcely causes rejection when it is administered to a human, and can contribute to enhancement of acquired immunity against an antigen, either. Further, it has not so far been attempted to stimulate a living body only with an immunostimulant carrying an immunostimulating substance on plasma (or serum)—derived proteins made into an insoluble solid by denaturation coagulation at a molecular level as a main carrier, i.e., as BRM, without simultaneously administering an antigen at the same site, and thereby enhance general immunoreactions.

It is also known that tuberculin, which is a typical substance that induces the type IV allergic reaction (also referred to as delayed type allergy, cell-mediated immunity, or tuberculin type reaction), is a very safe substance, even when it is repeatedly administered to a human (Non-patent document 14). In the type IV allergic reaction, cell-mediated immunoreactions are induced, and moreover, antibodies or complements, which are main players of the humoral immunoreactions, are not involved (Non-patent document 15). However, there is a problem that purified tuberculin is water-soluble, and therefore if it is administered into the inside of the body as it is, it is promptly diffused and disappears. Further, since purified tuberculin is not a tumor antigen, it is considered that tumor recurrence-preventing and curing effects cannot be expected for use of purified tuberculin alone.

Although purified tuberculin is easily adsorbed on a glass container, this adsorption can be prevented with serum albumin, and therefore it is understood that purified tuberculin strongly adsorbs to serum albumin (Non-patent documents 16 and 17). However, it is not known so far whether serum albumin shows sufficient adsorption ability to purified tuberculin when it is made into an insoluble solid by denaturation coagulation at a molecular level and a treatment with an crosslinking agent for proteins. Further, change of stimulating property of an antigen-presenting cell caused by purified tuberculin adsorbed on such an insoluble solid of albumin has not so far been examined at all, either. Similarly, it has not examined so far whether plasma (or serum)—derived proteins such as albumin made into an insoluble solid and made to carry an immunostimulating substance other than purified tuberculin change stimulating property of an immunocompetent cell.

Further, hemoglobin usually does not dissolve in the plasma, but when hemolysis occurs, it comes out of erythrocytes, and appears in the plasma, and it is widely known that hemoglobin has peroxidase-like activity. However, any immunostimulant using the peroxidase-like activity of hemoglobin is not known so far. Myoglobin, cytochrome, and catalase, which are hemoglobin-like proteins, also have peroxidase-like activity. However, any immunostimulant using the peroxidase-like activity of any of these hem proteins is not known so far, either.

PRIOR ART REFERENCES

Patent Documents

Patent document 1: Japanese Patent No. 4569946
Patent document 2: Japanese Patent No. 4688254
Patent document 3: Japanese Patent No. 5579586
Patent document 4: Japanese Patent No. 3492671
Patent document 5: Japanese Patent No. 4238279
Patent document 6: Japanese Patent No. 4176021

Non-Patent Documents

Non-patent document 1: Sakai H, Clinical Virology (Rinsho to Virus), 41(5):1-9, 2013
Non-patent document 2: Blog: Medical Note of EARL, world wide web//drmagician.exblog.jp/16073684
Non-patent document 3: Stills H F, Jr., Adjuvants and antibody production: Dispelling the myths associated with Freund's complete and other adjuvants, ILAR Journal, 46:280-293, 2005
Non-patent document 4: Kuroda E, Coban C, Ishii K J, Particulate adjuvant and innate immunity: Past achievements, present findings, and future prospects, Intern. Rev. Immunol., 32:209-220, 2013
Non-patent document 5: Disis M L, et al., Granulocyte-macrophage colony-stimulating factor: an effective adjuvant for protein and peptide-based vaccines, Blood, 88:202-210, 1996
Non-patent document 6: Ishii K, New development of adjuvant development and research, the 9th Health Sciences Council, Vaccination and vaccine subcommittee, Research and development, production, and distribution division meeting, Data 1, Jan. 30, 2015 (Heisei 27)
Non-patent document 7: Yutani S, et al. Phase II study of personalized peptide vaccination with both a hepatitis C virus-derived peptide and peptides from tumor-associated antigens for the treatment of HCV-positive advanced hepatocellular carcinoma patients, J. Immunol. Res., Article ID 473909, 2015, world wide web.hindawi.com/journals/jir/2015/473909/
Non-patent document 8: Hashimoto N, et al., Wilms tumor 1 peptide vaccination combined with temozolomide against newly diagnosed glioblastoma: safety and impact on immunological response, Cancer Immunol. Immunother., 64:707-16, 2015
Non-patent document 9: Kuang M, et al., Phase II randomized trial of autologous formalin-fixed tumor vaccine for postsurgical recurrence of hepatocellular carcinoma, Clin. Cancer Res., 10:1574-1579, 2004
Non-patent document 10: Kawashima I, et al., Suppression of postsurgical recurrence of hepatocellular carcinoma treated with autologous formalin-fixed tumor vaccine, with special reference to glypican-3, Clinical Case Reports, 3:444-447, 2015
Non-patent document 11: Ishikawa E, et al., A clinical trial of autologous formalin-fixed tumor vaccine for glioblastoma multiforme patients, Cancer Sci., 98:1226-1233, 2007
Non-patent document 12: Muragaki Y, et al., Phase I/IIa Trial of Autologous Formalin-fixed Tumor Vaccine Concomitant with Fractionated Radiotherapy for Initially-Diagnosed Glioblastoma, J. Neurosurg., 115:248-255, 2011
Non-patent document 13: Ishikawa E, et al., Phase I/IIa trial of fractionated radiotherapy, temozolomide, and autologous formalin-fixed tumor vaccine for newly diagnosed glioblastoma, J. Neurosurg., 121:543-553, 2014

Non-patent document 14: Kunins H V, et al., Validity of a self-reported history of a positive tuberculin skin test—A prospective study of drug users, J. Gen. Intern. Med., 19:1039-1044, 2004

Non-patent document 15: Ministry of Health, Labor and Welfare homepage, Introduction of allergy, Chapter 1, world wide web.mhlw.go.jp/new-info/kobetu/kenkou/ryumachi/dl/jouhou01-17.pdf Non-patent document 16: Guld J, Standardization and stability of purified tuberculin, American Review of Respiratory Disease, 80(2), pp.255-256, 1959

Non-patent document 17: Landi S, Held H R, Tseng M C, Evaluation of various substances to prevent adsorption of tuberculin purified protein derivative (PPD) to glass surfaces, Bull. Org. mond. Sant. Bull. Wld. Hlth. Org., 43:91-106, 1970

Non-patent document 18: Kurosaka K, Watanabe N, Kobayashi Y, Production of proinflammatory cytokines by phorbol myristate acetate-treated THP-1 cells and monocyte-derived macrophages after phagocytosis of apoptotic CTLL-2 cells, J. Immunol., 161:6245-6249, 1998

Non-patent document 19: Hu P Q, et al., *Escherichia coli* expressing recombinant antigen and listeriolysin 0 stimulate class I-restricted CD8+ T cells following uptake by human APC, J. Immunol., 172:1595-1601, 2004

Non-patent document 20: Brett S J, Rhodes J, Liew F Y, Tite J P, Comparison of antigen presentation of influenza A nucleoprotein expressed in attenuated AroA-*Salmonella typhimurium* with that of live virus, J. Immunol., 150: 2869-2884, 1993

Non-patent document 21: Oliveira M M, Charlab R, Pessolani M C, *Mycobacterium bovis* BCG but not *Mycobacterium leprae* induces TNF-alpha secretion in human monocytic THP-1 cells, Mem. Inst. Oswaldo. Cruz., 96(7):973-978, 2001

Non-patent document 22: Gordon S, The macrophage: past, present and future, Eur. J. Immunol., 37: Suppl 1:S9-17, 2007

Non-patent document 23: Chang Z L. Recent development of the mononuclear phagocyte system: in memory of Metchnikoff and Ehrlich on the 100th Anniversary of the 1908 Nobel Prize in Physiology or Medicine, Biol. Cell., 101 (12):709-721, 2009

Non-patent document 24: Cho Y S et al., Deciphering the proteome of the in vivo diagnostic reagent "purified protein derivative" from *Mycobacterium tuberculosis*, Proteomics, 12 (7):979-991, 2012, doi:10.1002-/pmic.201100544

Non-patent document 25: Najjam S, et al., Further characterization of the binding of human recombinant interleukin 2 to heparin and identification of putative binding sites, Glycobiology, 8:509-516, 1998

Non-patent document 26: DAKO Educational IHC Guidebook, Immunohistochemical Staining Methods, Sixth Edition, Chapter 15, ed. Tayor C R and Rudbeck L, 2013, world wide web.dako.com

SUMMARY OF THE INVENTION

Object to be Achieved by the Invention

An object of the present invention is to provide a highly safe immunostimulant having such high effectiveness that it can strongly stimulate an antigen-presenting cell, and showing reduced toxicity to living bodies.

Means for Achieving the Object

The inventors of the present invention conducted various researches in order to achieve the aforementioned object. As a result, they observed that administration of a material prepared by solidifying plasma-derived proteins such as albumin, or the like by denaturation coagulation to a living body does not induce rejection, and also found that a complex prepared by making a carrier containing albumin or the like solidified by such denaturation coagulation as mentioned above carry a protein having a peroxidase-like activity such as hemoglobin has a high immunostimulating ability. They further found that the aforementioned carrier maintains a high adsorption property for immunostimulating substances such as purified tuberculin, and by making the aforementioned complex carry an immunostimulating substance such as purified tuberculin, more potent immunostimulating ability can be achieved. The present invention was accomplished on the basis of such findings.

The inventors of the present invention thus provide the following inventions.

[1] A complex comprising a carrier containing a plasma-derived protein or serum-derived protein solidified by denaturation coagulation, and a protein having a peroxidase-like activity and carried by the carrier.

[2] The complex according to [1] mentioned above, wherein the protein having a peroxidase-like activity is carried in a substantially undenatured state or a denatured state.

[3] The complex according to [1] mentioned above, wherein the protein having a peroxidase-like activity is carried in a state that it is solidified by denaturation coagulation together with the plasma-derived protein or serum-derived protein.

[4] The complex according to any one of [1] to [3] mentioned above, wherein the protein having a peroxidase-like activity is hemoglobin or myoglobin.

[5] The complex according to any one of [1] to [4] mentioned above, which further carries one kind or two or more kinds of immunostimulating substances.

[6] The complex according to [5] mentioned above, wherein the immunostimulating substance consists of one kind or two or more kinds of substances selected from the group consisting of a purified tuberculin, a BCG bacteria extract, a cytokine, a Toll-like receptor ligand, a NOD-like receptor agonist, a RIG-like receptor agonist, a C type lectin receptor agonist, an exogenous DNA that binds with a cyclic GMP-AMP synthase, an alarmin, an antigen, and an antibody.

[7] An immunostimulant containing the complex according to any one of [1] to [6] mentioned above.

[8] An immunostimulating composition containing the immunostimulant according to [7] mentioned above, and albumin-heparin coacervate precipitates.

[9] The immunostimulating composition according to [8] mentioned above, wherein the albumin-heparin coacervate precipitates are albumin heparin coacervate precipitates adsorbed with a cytokine.

[10] The immunostimulating composition according to [9] mentioned above, wherein the cytokine consists of one kind or two or more kinds of substances selected from the group consisting of granulocyte-macrophage colony-stimulating factor, interleukin-2, and interferon γ.

[11] A medicament for use in therapeutic and/or prophylactic treatment of a disease, which comprises a combination of the immunostimulant according to [7] mentioned above or the immunostimulating composition according to [8] mentioned above, and an immunoreaction-suppressing action inhibitor.

[12] The medicament according to [11] mentioned above, which is for use in therapeutic treatment of a malignant tumor and/or prophylactic treatment of recurrence or metastasis of a malignant tumor.

[13] The medicament according to [11] or [12] mentioned above, wherein the immunoreaction-suppressing action inhibitor is an immune Checkpoint inhibitor.

[14] The medicament according to [13] mentioned above, wherein the immune checkpoint inhibitor consists of one kind or two or more kinds of antibodies selected from the group consisting of an anti-PD-1 antibody, an anti-PD-L1 antibody, an anti-PD-L2 antibody, an anti-CTLA-4 antibody, an anti-CD40 antibody, an anti-CD137 antibody, an anti-OX40 antibody, an anti-TGF-β antibody, an anti-LAG3 antibody, an anti-B7-H3 antibody, an anti-B7-H4 antibody, an anti-TIM3 antibody, an anti-CD96 antibody, and an anti-TIGIT antibody.

[15] A vaccine for use in prophylactic treatment of a disease, which comprises a combination of the immunostimulant according to [7] mentioned above or the immunostimulating composition according to [8] mentioned above, and an antigen.

[16] The vaccine according to [15] mentioned above, wherein the antigen is a tumor antigen.

[17] The vaccine according to [16] mentioned above, which is for use in prophylactic treatment of recurrence or metastasis of a malignant tumor.

[18] A method for activating immunity in a mammal including human, which comprises the step of administrating an effective amount of the immunostimulant according to [7] mentioned above or the immunostimulating composition according to [8] mentioned above to the mammal including human.

[19] A method for therapeutic and/or prophylactic treatment of a disease, preferably a malignant tumor, in a mammal including a human, which comprises the step of administrating an effective amount of a combination of the immunostimulant according to [7] mentioned above or the immunostimulating composition according to [8] mentioned above, and an immunoreaction-suppressing action inhibitor to the mammal including human.

[20] A method for prophylactic treatment of recurrence or metastasis of a malignant tumor in a mammal including a human, which comprises the step of administrating an effective amount of a combination of the immunostimulant according to [7] mentioned above or the immunostimulating composition according to [8] mentioned above, and an antigen to the mammal including human.

Effect of the Invention

The complex of the present invention comprising a carrier containing a plasma-derived protein or serum-derived protein solidified by denaturation coagulation, and a protein having a peroxidase-like activity and carried by the carrier, preferably such a complex as mentioned above, wherein the protein having a peroxidase-like activity such as hemoglobin is carried in a state that it is solidified by denaturation coagulation together with the plasma-derived protein or serum-derived protein such as albumin, has an immunostimulating action, and can effectively stimulate an antigen-presenting cell, and therefore it is useful as an immunostimulant for therapeutic treatment of a disease such as tumor, as well as prophylactic treatment for postoperative recurrence or metastasis of a malignant tumor. In a more preferred embodiment, the complex is made to carry an immunostimulating substance such as purified tuberculin, and thereby it can be used as a potent immunostimulant.

The immunostimulant provided by the present invention is safe, and does not induce any problematic adverse event of grade 3 or higher according to the Common Terminology Criteria for Adverse Events (CTCAE) version 4.0 (Japanese translation thereof as JCOG version is published by Japan Clinical Oncology Group) used in human clinical medicine, and therefore it can be clinically safely used.

MODES FOR CARRYING OUT THE INVENTION

Figure 1:
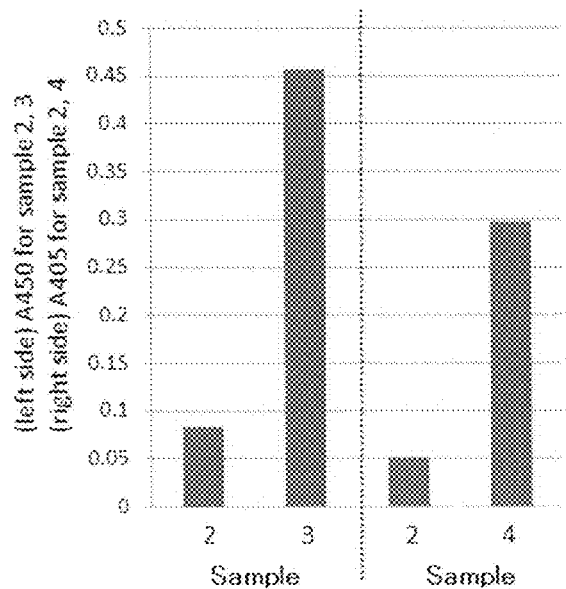
FIG. 1 A graph showing that Sample 2 (denaturation coagulation-solidified plasma carrier), Sample 3 (denaturation coagulation-solidified plasma carrier adsorbed with undenatured hemoglobin), and Sample 4 (denaturation coagulation-solidified plasma carrier adsorbed with undenatured myoglobin) used in Example 1 had an antigen-presenting cell-stimulating action.

The immunostimulant of the present invention has a form of a complex comprising a carrier obtained by solidifying a plasma-derived protein or serum-derived protein by denaturation coagulation, desirably such a carrier solidified into a more stable solid state by a treatment with a crosslinking agent, which is made to carry a protein having a peroxidase-like activity, and it can also be used in a form of such a complex as mentioned above, which is made to further carry an immunostimulating substance. The immunostimulant of the present invention can be used as it is as BRM to be administered to the inside of the body, and it can also be used as an immunoadjuvant for administration to a living body together with an antigen.

In this specification, the term "immunostimulant" and synonyms thereof (for example, "immunostimulating substance" and the like) should be construed in the broadest senses thereof so as to encompass those showing a direct stimulating action on an immunoreaction specific to a specific antigen, as well as those showing an indirect stimulating action on an antigen-nonspecific immunoreaction irrespective of the presence or absence of an antigen.

The "immunostimulant" may be (a) an "immunoadjuvant" that is used together with an antigen, and expected to enhance an immunoreaction specific to the antigen, (b) BRM that is used without an antigen, and is used for general activation of immunological competence, or the like. The BRM of (b) may be (b-1) an "immunoreaction enhancer" that directly stimulates an immunoreaction pathway, which may be only a part thereof, or (b-2) an "immunoreaction-suppressing action inhibitor" that indirectly stimulating immunity by an action of conversely inhibiting an immunoreaction-suppressing action based on inhibition of an immunoreaction pathway. The immunostimulant of the present invention can be used as (a) and (b-1), as well as (b-2) in the form of being made to carry the "immunoreaction-suppressing action inhibitor".

The inventors of the present invention found that a complex that can be obtained by preparing an insoluble carrier by solidifying a protein dissolved in the plasma or serum (plasma-derived protein or serum-derived protein) such as albumin by denaturation coagulation at a molecular level, and making the carrier carry a protein having a peroxidase-like activity such as hemoglobin and myoglobin is useful as an immunostimulant, and this complex made to further carry an immunostimulating substance such as purified tuberculin has an effect of more strongly promoting production of a cytokine (such as tumor necrosis factor alpha, TNFα) by antigen-presenting cells serving as the origin of immunoreactions.

The carrier provided by the present invention, which contains a plasma-derived protein or serum-derived protein solidified by the denaturation coagulation, can be obtained by solidifying a plasma-derived or serum-derived protein such as albumin by denaturation coagulation, and it is generally provided in the form of water-insoluble microparticles having a particle diameter of 70 μm or smaller.

The method for solidifying a plasma-derived protein or serum-derived protein, which is originally water-soluble, by denaturation coagulation at molecular level, to prepare a carrier preferably in the form of microparticles is not particularly limited, and any method known to those skilled in the art can be used. As the means for the denaturation coagulation, for example, thermal denaturation, acid treatment, organic solvent treatment, surfactant treatment, and the like are well known to those skilled in the art, and these treatments can be used alone, or two or more of them can be used in combination. For example, when a method of denaturing protein molecules by heating to coagulate them is used, for example, a heat treatment at 100° C. or higher can be employed, but the temperature is not limited to be within such a temperature range. The method for preparing the carrier in the form of microparticles is not particularly limited, either, and any method available for those skilled in the art may be used. For example, it is preferable to prepare the carrier in the form of microparticles having a desired particle diameter by mechanically grinding the solid obtained by denaturation coagulation, and passing the ground solid through a mesh, filter or the like having an appropriate pore diameter, but the method is not limited to such a method.

In such an embodiment where the solid in the form of microparticles is used as the carrier of an immunostimulant, it is generally undesirable that the carrier in the form of solidified microparticles are solubilized in an aqueous solvent, therefore soluble portions can be removed from the resulting solid in the form of microparticles, and the portion that remains as an insoluble solid can be used as the carrier. For such a purpose, the solidified carrier may be washed with water or a hydrophilic solvent such as ethanol, acetone, and the like as required.

In another embodiment, the solidified carrier can be treated with an intermolecular crosslinking agent for proteins to prepare the carrier as a more stabilized insoluble solid. The type of the intermolecular crosslinking agent for proteins is not particularly limited, and those well known to those skilled in the art can be used in a well-known manner. There can be used, for example, formaldehyde, formalin, paraformaldehyde, glutaraldehyde, 1-ethyl-3-(3-dimethylaminopropyl)-carbodiimide (EDC), and the like. For example, a method of immersing the carrier in a neutral 10% formalin solution at room temperature for 3 days or longer, or the like is preferred. Further, for example, when an aqueous solution of EDC is added to the carrier at a final concentration of 0.8 to 1.5 mg/ml with stirring using a vortex mixer, and they are left standing at room temperature for 15 minutes, sufficiently stable crosslinking is formed between the protein molecules in the solidified carrier. However, the means for crosslinking is not limited to the aforementioned specific conditions or specific intermolecular crosslinking agent for proteins. The immunostimulant prepared in such a manner as described above, preferably such an immunostimulant sufficiently crosslinked, is not dissolved, even if it is washed with water, and can be preferably used as the carrier in the immunostimulant of the present invention.

The carrier containing the plasma-derived protein or serum-derived protein solidified by denaturation coagulation provided by the present invention can be made to carry a protein having a peroxidase-like activity. This protein may be carried by the carrier in a substantially undenatured state, or it may be carried in a denatured state. As the protein having a peroxidase-like activity, for example, hem proteins can be used, and more specifically, myoglobin, cytochrome, catalase, and the like, as well as hemoglobin, can be used.

The method for making the carrier carry the protein having a peroxidase-like activity is not particularly limited, and an arbitrary method can be employed so long as a method is chosen that can attain a state that the protein having a peroxidase-like activity is carried with a sufficient strength, and they are integrated. For example, as the means for making it carry the protein, an adsorption reaction may be used. The term of adsorption should not be construed in any limitative way in any sense, and should be construed in the broadest sense thereof. By making the aforementioned carrier adsorb a protein having a peroxidase-like activity, a complex in a state that the protein is carried on the carrier in a substantially undenatured state can be prepared. As an alternative method for making it carry the protein, the protein having a peroxidase-like activity can also be fixed to the carrier with a covalent bond while the protein is maintained in a substantially undenatured state by a treatment using a chemical means such as a crosslinking agent.

Since a hem protein such as hemoglobin may have a peroxidase-like activity even in a denatured state, the protein having a peroxidase-like activity may also be carried by the aforementioned carrier in a denatured state. For example, when a plasma-derived or serum-derived protein such as albumin is solidified by denaturation coagulation, this protein and the protein having a peroxidase-like activity such as hemoglobin can be made to coexist by such a means as mixing to prepare a solid containing the plasma-derived or serum-derived protein and the protein having a peroxidase-like activity both of which are in a denatured state. In this specification, the term "carry" may also mean to have the protein in a state that both the protein having a peroxidase-like activity and the protein that forms the carrier such as albumin are denatured and integrally solidified, and it should not be construed in any limitative way in any sense, and should be construed in the broadest sense thereof.

The complex in the form of a solid obtained by denaturing albumin used as the plasma-derived or serum-derived protein and hemoglobin used as the protein having a peroxidase-like activity in a state that these proteins are mixed constitutes a preferred embodiment of the present invention, and microparticles obtained by mixing hemoglobin with serum albumin, coagulating them by heat denaturation, subjecting them to a formalin fixation treatment, and making them into microparticles (hemoglobin-albumin microparticles, HAMP) constitute a particularly preferred embodiment of the present invention. Although the particle diameter of the microparticles is not particularly limited, it is, for example, in the range of 200 to 0.01 µm. They usually preferably have such a particle diameter that they can pass through a mesh or filter having a pore diameter of 70 µm, but the particle diameter is not limited to any specific size. It is widely known to those skilled in the art that any living organisms cannot survive in an aqueous solvent containing a sufficient amount of an intermolecular crosslinking agent for proteins. Accordingly, even if an unknown harmful organism is contained in the plasma-derived or serum-derived protein as the raw material, it can be made to contain no organism by a treatment with an intermolecular crosslinking agent for proteins (typical example is a treatment consisting only of immersion in a neutral 10% formalin solution), and therefore safety of the immunostimulant of the present invention can be enhanced by the aforementioned treatment.

Since the aforementioned complex has an immunostimulating action by itself, it can be used as an immunostimulant. However, it can be used as an immunostimulant also in a state that, for example, it is made to further carry one kind or two or more kinds of immunostimulating substances such as purified tuberculin. As the purified tuberculin, for example, total proteins of purified tuberculin can be used, or a part or all of soluble proteins prepared from tuberculin by a method well known to those skilled in the art can be used. The ratio of the immunostimulating substance carried on the aforementioned complex is not particularly limited, and it may be appropriately selected from such a range that the immunostimulating substance can be adsorbed on the complex. As the immunostimulating substance, there can be used, for example, BCG bacteria extract, cytokine, Toll-like receptor ligand, NOD-like receptor agonist, RIG-like receptor agonist, C type lectin receptor agonist, exogenous DNA that binds to cyclic GMP-AMP synthase, alarmin, antigen, antibody and the like, as well as purified tuberculin.

As a means for the carrying other than adsorption, for example, by mixing beforehand the plasma-derived or serum-derived proteins such as albumin, the protein having a peroxidase-like activity such as hemoglobin, and a soluble protein such as purified tuberculin as an immunostimulating substance having an immunoadjuvant activity, and obtaining a complex solidified by denaturation coagulation from the above mixture in the same manner as described above, there can be produced an immunostimulant comprising the protein having a peroxidase-like activity and the immunostimulating substance having an adjuvant activity such as purified tuberculin soluble protein carried by the plasma-derived or serum-derived protein.

The immunostimulant may be the aforementioned immunostimulant comprising the protein having a peroxidase-like activity and the immunostimulating substance having an adjuvant activity such as a purified tuberculin soluble protein, which is made further carry an insoluble protein. As the insoluble protein, for example, a biodegradable insoluble protein can be used, and more specifically, collagen and the like can be used, but it is not limited to these examples. In such an embodiment, any protein may be used so long as an insoluble protein that is decomposed in the living body is chosen.

The immunostimulant of the present invention can also be used as an immunostimulating composition containing albumin-heparin coacervate precipitates in combination. As the albumin-heparin coacervate precipitates, for example, albumin-heparin coacervate precipitates adsorbed with a cytokine can be used. As the cytokine, for example, one kind or two or more kinds of substances selected from the group consisting of granulocyte-macrophage colony-stimulating factor (GM-CSF), interleukin-2 (IL-2), and interferon γ (IFNγ, also referred to as "IFNg" in this specification) can be used, but the cytokine is not limited to these examples.

When the immunostimulant of the present invention is used for therapeutic and/or prophylactic treatment of a disease, it can be made into a pharmaceutical preparation by mixing pharmacologically acceptable carriers, excipients, additives, and the like, and can be administered to a mammal including human as a pharmaceutical composition. When the immunostimulant of the present invention does not carry any immunostimulating substance such as purified tuberculin, by mixing an immunostimulating substance such as purified tuberculin separately made into a pharmaceutical preparation at the time of use, they can be simultaneously administered. Alternatively, a treatment can be performed by separately administering them at the same site so that they coexist in the same local part in the living body. When the immunostimulant of the present invention carries one kind or two or more kinds of immunostimulating substances, it can be mixed with an immunostimulating substance of a type different from those of the carried immunostimulating substances at the time of use, and they can be simultaneously administered. Alternatively, a treatment can be performed by separately administering them at the same site so that they coexist in the same local part in the living body.

The immunostimulant of the present invention can be used as a general immunoadjuvant. By simply mixing it with an antigen, and administering them to the inside of a body of a mammal including human, systemic immunoreactions to the antigen can be induced. When the antigen consists of a tumor tissue, tumor cell, tumor cell ingredient, and/or tumor antigen peptide, it can be used as a tumor vaccine. For example, if a mixture of lysed cancer cells (lysate) separated from a patient and the immunostimulant of the present invention is injected to the patient, antitumor immunoreactions against the specific cancer cells can be induced in the body of the patient. Similarly, if the antigen is derived from a microorganism that induces an infectious disease, it can be used as an ordinary vaccine for prophylaxis of infectious disease. However, the method for use of the immunostimulant of the present invention is not limited to the aforementioned methods, and any of the usual methods using an immunoadjuvant may be used.

Further, by denaturing a tumor tissue in the body of a patient with a physical means, and then administering the immunostimulant of the present invention into the denatured tissue, there is attained a state that the tumor antigen contained in the tumor tissue and the immunostimulant of the present invention coexist in the topical part, and thus in situ vaccination is enabled, in which antitumor immunoreactions against living tumor cells remaining in the body of the patient are induced. Although the physical means for denaturing the tumor tissue is not particularly limited, for example, such means as microwave irradiation, radiofrequency coagulation method, freeze coagulation method, electrotome heating, hot water injection, alcohol injection, embolization method, radiation irradiation, laser beam irradiation, and ultrasonic disruption can be used independently, or as an appropriate combination of two or more of them. However, the physical means is not limited to these examples, and any means that can induce cell death of tumor cells in the tumor tissue can be used.

For example, if a tumor tissue is coagulated with heating by microwave irradiation, and the immunostimulant of the present invention is administered into the coagulated tissue, antitumor immunoreactions can be induced against living tumor cells in the inside of the tumor tissue and the surrounding parts thereof. When the immunostimulant of the present invention is administered, it is also preferable to further simultaneously administer a purified tuberculin solution, a cytokine that stimulates immunoreactions, or a slow release preparation of a cytokine. However, the method for administering the immunostimulant of the present invention is not limited to the aforementioned schemes, and any method may be employed so long as the immunostimulant of the present invention is uptaken into antigen-presenting cells gathering in the denatured tumor tissue together with the tumor antigens contained in the denatured tumor tissue, or there is given an environment where the immunostimulant of the present invention can directly stimulate the antigen-presenting cells.

Further, the immunostimulant of the present invention and immunocompetent cells can also be mixed out of a body of a patient, and then administered to the inside of the body of the patient to stimulate immunoreactions in the living body. As the immunocompetent cells, dendritic cells, macrophages, monocytes, B lymphocytes, T lymphocytes, natural killer cells, and the like can be preferably used, but the immunocompetent cells are not limited to these examples. In the aforementioned method, two or more kinds of immunocompetent cells may be used in combination.

As another aspect, a vaccine containing the immunostimulant of the present invention as an immunoadjuvant is provided. The vaccine can be administered together with an antigen as a disease factor substance, preferably an antigen derived from an exogenous organism such as a pathogenic microbe, a viral antigen, or a tumor antigen, and immunocompetent cells may be further mixed simultaneously. The antigen is preferably derived from the patient, but an allogenic antigen of the same type can also be used. For example, a tumor tissue and/or tumor cells extracted from another patient can also be used together by mixing, and a vaccine obtained in such a manner can be administered to a tumor patient to treat a tumor such as malignant tumor. Since the aforementioned vaccine can effectively stimulate cell-mediated immunoreactions required for treatment of a tumor, it enables, for example, prevention of metastasis or postoperative recurrence of a malignant tumor.

In a preferred embodiment, the immunostimulant of the present invention can also be made to carry an immunoreaction-suppressing action substance such as an immune checkpoint-inhibiting antibody, and according to such an embodiment, the immunostimulant or the tumor vaccine can be used for the purpose of more effective therapeutic treatment of a malignant tumor, as well as prophylactic treatment of a malignant tumor, prophylactic treatment of metastasis of a malignant tumor, and the like. As the immune checkpoint-inhibiting antibody, there can be used, for example, one kind or two or more kinds of antibodies selected from the group consisting of anti-PD-1 antibody, anti-PD-L1 antibody, anti-PD-L2 antibody, anti-CTLA-4 antibody, anti-CD40 antibody, anti-CD137 antibody, anti-OX40 antibody, anti-TGF-6 antibody, anti-LAG3 antibody, anti-B7-H3 antibody, anti-B7-H4 antibody, anti-TIM3 antibody, anti-CD96 antibody, and anti-TIGIT antibody, but the antibody is not limited to these examples.

It is widely known by those skilled in the art that tumor antigens contained in tumor cells naturally occurring in the living bodies generally show low antigenicity, therefore they cannot induce antitumor immunoreactions in the living bodies in many cases, and therefore allows tumor proliferation. However, by using the immunostimulant of the present invention as an immunoadjuvant, effective antitumor immunoreactions can be induced for such a tumor antigen showing low antigenicity as mentioned above. Similarly, even for other disease factor substances derived from living bodies and showing low antigenicity, by using the immunostimulant of the present invention as an immunoadjuvant, immunoreactions can be induced for such disease factor substances showing low antigenicity.

Furthermore, if the immunostimulant of the present invention is used, antigen-presenting cells can be stimulated, and GM-CSF considered to be necessary for survival and proliferation of the antigen-presenting cells can be made to be released from the antigen-presenting cells themselves. Therefore, there can be achieved the activation and maintenance of such an activated state of the antigen-presenting cells themselves, on which GM-CSF acts as an autocrine cell growth factor, and neighboring antigen-presenting cells, on which GM-CSF acts as a paracrine cell growth factor. Since this is one of the characteristics of BRM that raises immunological competence of living bodies, the immunostimulant of the present invention is useful as BRM.

EXAMPLES

Hereafter, the present invention will be still more specifically explained with reference to examples. However, the scope of the present invention is not limited by the following examples.

The terms and concepts used for the explanations and definitions of the present invention are based on the meanings of terms conventionally used in this field, and techniques used for implementing the present invention can be easily and correctly carried out by those skilled in the art on the basis of the descriptions of published references and the like, except for those of which citation sources are especially indicated. Various analyses, and the like were performed according to the methods described in instructions, catalogues, and the like of the analytical instruments, reagents, and kits used.

TABLE 1

Abbreviation table

| Abbreviation | |
|---|---|
| 3% medium | RPMI1640 culture medium containing 3% heat-treated fetal bovine serum |
| BCGext | BCG bacteria extract |
| BRM | Biological response modifier |
| CTCAE | Common terminology criteria for adverse events |
| CTL | Cytotoxic T cell |
| ELISA | Enzyme-linked immunosorbent assay |
| FCA | Freund's complete adjuvant |
| GM-CSF | Granulocyte-macrophage colony-stimulating factor |
| HAMP | Hemoglobin-albumin microparticle solidified by denaturation coagulation |
| hGM-CSF | Human granulocyte-macrophage colony-stimulating factor |
| hGM-CSF-HAMP | HAMP adsorbed with hGM-CSF |
| hIFNg | Human interferon γ |
| hIFNg-HAMP | HAMP adsorbed with hIFNg |
| hIL-2 | Human interleukin-2 |
| hIL-2-HAMP | HAMP adsorbed with hIL-2 |
| HSA | Human serum albumin |
| IFA | Freund's incomplete adjuvant |
| IL-2 | Interleukin-2 |
| MHC | Major histocompatibility complex |
| nega-TuMP | Heparin-albumin coacervate precipitates (in the form of microparticles) not containing purified tuberculin |
| OVA | Ovalbumin |
| PBS(−) | Dulbecco's $Ca^+$ and $Mg^+$-free phosphate buffer |
| PMA | Phorbol 12-myristate 13-acetate |
| PPD | Purified tuberculin |
| PPD-HAMP | HAMP adsorbed with PPD |
| SAv-HRP | Streptavidin-horseradish peroxidase |
| SAv-ALP | Streptavidin-alkaline phosphatase |
| TNFα | Tumor necrosis factor alpha (also simply referred to as TNF) |

Example 1: Preparation of Carrier Containing Denaturation Coagulation-Solidified Plasma, and Antigen-Presenting Cell-Stimulating Effect of Undenatured Hemoglobin-Adsorbed Complex or Undenatured Myoglobin-Adsorbed Complex It is known that if differentiation of cells of the human macrophage-like cell line THP-1 is induced by adding phorbol 12-myristate 13-acetate (PMA) to act on them during cultivation, they not only show phagocytic ability (Non-patent document 18), but also acquire antigen-presenting ability, and become antigen-presenting cells (Non-patent document 19). Further, if the cells are pretreated with human interferon γ (IFNg), which is a cytokine, the antigen-presenting ability thereof for T-cells is enhanced (Non-patent document 20). THP-1 cells that have differentiated and exhibited phagocytosis produce TNFα (Non-patent document 21). The production of TNFα indicates activation of macrophages (or antigen-presenting cells), and it is known that activation of macrophages (or antigen-presenting cells) in the inside of the body is the start point of the following inflammatory reactions and immunoreactions (Non-patent documents 22 and 23).

Therefore, if differentiation of the THP-1 cells into antigen-presenting cells is induced, then they are allowed to phagocytize a certain solid, and amount of produced TNFα is measured, the inflammatory reaction and immunoreaction-stimulating action of the solid in the inside of the body can be measured in a cell culture system outside the body.

(1) Method for Preparing Samples for Bioassay

From adult volunteers, blood was collected as heparinized blood in a conventional manner, and plasma was obtained by centrifugation in a conventional manner. This plasma (2.25 mL) was coagulated by a heat treatment at 110° C. for 5 minutes, and then roughly ground with a spatula. A marketed 10% neutral buffered formalin solution (20 mL) was added to the plasma, and they were left at room temperature for 3 days to attain formalin fixation. The fixed ground product was washed with physiological saline, and then ground for 10 minutes on a widely used tissue-grinding machine (Tissue Lyser II, produced by Qiagen), on which a microtube can be set. The fragments made into microparticles were passed through a mesh having a pore diameter of 70 μm, washed by centrifugation with a sufficient volume of physiological saline, sterilized by immersion in ethanol, and then washed again by centrifugation with a sufficient volume of physiological saline. An appropriate volume of physiological saline was added to the fragments and suspend them, so that the volume ratio of the fragments was 25 v/v % after centrifugation at 3,000 rpm (maximum acceleration was 1580 G) for 15 minutes on a desktop centrifuge, to prepare Sample 2 for bioassay "denaturation coagulation-solidified plasma carrier suspension".

Human hemoglobin (117379-5G, produced by SIGMA) or horse myoglobin (M0630, produced by SIGMA) was suspended at 4 w/v % in purified water, and dissolved by stirring at room temperature for 2 hours, the insoluble matter was removed by centrifugation at 3,000 rpm for 15 minutes, and the supernatant was sterilized by filtration through a membrane filter having a pore diameter of 0.22 μm. This solution (36 μL) and the denaturation coagulation-solidified plasma carrier suspension (264 μL) were mixed, and the mixture was stirred at room temperature for 2 hours, and centrifuged at 4° C. and 12,000 rpm (maximum acceleration was 11,000 G), for 5 minutes on a high-speed microcentrifuge to obtain precipitates. The precipitates were washed by centrifugation with a sufficient volume of physiological saline, and physiological saline (198 μL) was added to the precipitates to suspend them to prepare Sample 3 for bioassay "undenatured hemoglobin-adsorbed denaturation coagulation-solidified plasma carrier suspension", and Sample 4 for bioassay "undenatured myoglobin-adsorbed denaturation coagulation-solidified plasma carrier suspension".

(2) Method for Bioassay with Antigen-Presenting Cells

A 500,000 cells/mL suspension of the human macrophage-like cell line THP-1 cells maintenance-cultured in a conventional manner was prepared in a culture medium. The culture medium was the RPMI1640 culture medium containing 3% fetal bovine serum heat-treated in a conventional manner (henceforth referred to as "3% medium"). To the suspension, a phorbol 12-myristate 13-acetate (PMA) solution (prepared by dissolving PMA produced by SIGMA at 1.62 mM in dimethyl sulfoxide) was added at a final concentration of 0.16 μM. The cell suspension was inoculated in wells of a 24-well plate in a volume of 0.5 mL/well, and culture was performed for 4 days to induce differentiation of the THP-1 cells into antigen-presenting cells. Those referred to as antigen-presenting cells in the following examples are cells obtained by differentiation induced by this method.

After the differentiation-inducing culture, the medium was changed for a culture medium for assay (3% medium containing 0.016 μM PMA and 0.5 ng/mL of human interferon γ (hIFNg)), and the culture was continued overnight. Then, the medium was changed for fresh culture medium for assay, each of the following samples for bioassay was added to the culture medium for assay in a volume of 0.5 mL/well, and culture was carried out for 22 hours (henceforth referred to as "assay culture").
Sample 1: Physiological saline, 32 μL (TNFα production amount obtained with this sample was used as the blank value)
Sample 2: Denaturation coagulation-solidified plasma carrier suspension, 32 μL
Sample 3: Undenatured hemoglobin-adsorbed denaturation coagulation-solidified plasma carrier suspension, 32 μL
Sample 4: Undenatured myoglobin-adsorbed denaturation coagulation-solidified plasma carrier suspension, 32 μL The culture medium obtained after the assay culture was centrifuged at 4° C. and 12,000 rpm (maximum acceleration was 11,000 G) for 5 minutes on a cooled high-speed microcentrifuge, the supernatant was collected, and the concentration of tumor necrosis factor α (TNFα) in the supernatant was measured. Two or three wells were used for one kind of sample, and average values were used as data.
(3) Method for Measuring TNFα

A marketed TNFα measurement kit based on ELISA (OptEIA Set Human TNF produced by BD Biosciences, Cat. No. 555212) was used. The details of the method of ELISA were as described in the instruction attached to this kit. In this measurement operation, washing by adding a large excess volume of a washing solution containing the surfactant Tween 20 to wells for ELISA is repeated. In this experiment, the washing step was repeated 5 times after addition of the centrifugation supernatant obtained from the collected culture medium to the wells for ELISA coated with the primary antibody for capture, and 7 times after the addition of streptavidin-horseradish peroxidase (this is included in the kit, henceforth abbreviated as SAv-HRP) or streptavidin-alkaline phosphatase (produced by Promega, Cat. No. V5591, abbreviated as SAv-ALP), which was additionally added to the secondary antibody for detection, and accordingly, the washing was repeated 12 times in total. Therefore, even if microparticles of the denaturation coagulation-solidified plasma carrier were contaminated in the centrifugation supernatant obtained from the collected culture medium, they could be fully removed by the washing. In fact, when ELISA was performed with this kit for TNFα measurement intentionally without adding SAv-HRP at the time of the measurement of TNFα in the centrifugation supernatant of the collected culture medium, measured value of TNFα was the blank level, and therefore sufficient removal from the centrifugation supernatant of the collected culture medium was confirmed on the basis of this fact.

Since the concentration of the standard TNF attached to this kit and final color reaction show very good linearity, the final data as the absorbance values obtained with a plate reader (Biotrak II, Amersham Biosciences) are shown in the graphs as they are after subtraction of the blank value of Sample 1. When SAv-HRP was used (used for Samples 1, 2, and 3), A450 values obtained by using the widely used marketed TMB substrate solution and 2N H2SO4 reaction stop solution are presented. The A450 value of 1.0 corresponds to 60 pg/mL of the standard TNF attached to the kit. When SAv-ALP was used (used for Samples 1, 2, and 4 as the separate experiments), A405 values obtained by using a substrate solution prepared by dissolving p-nitrophenyl phosphate marketed for the activity measurement of alkaline phosphatase at 2 mg/mL, and 0.5N NaOH reaction stop solution are presented. This method is also one of the conventional methods for those skilled in the art. The conditions of this measurement were determined so that the A405 value for 240 pg/mL of the standard TNF attached to the kit should be 0.3. The results for the TNFα production amount are shown in FIG. 1. The values are those obtained after subtraction of the blank value (Sample 1). The left two bars shown in the graph of FIG. 1 indicate the results obtained by using SAv-HRP for Samples 2 and 3, and the right two bars indicate the results obtained by using SAv-ALP for Samples 2 and 4 in the separate experiments.

These results revealed that the denaturation coagulation-solidified plasma carrier of Sample 2 has an antigen-presenting cell-stimulating action, and Sample 3, which was the denaturation coagulation-solidified plasma carrier adsorbed with undenatured hemoglobin, has a stronger antigen-presenting cell-stimulating action. It was also revealed that Sample 4 adsorbed with undenatured myoglobin also has a potent antigen-presenting cell-stimulating action.

Example 2: Antigen-Presenting Cell-Stimulating Effect of Denaturation Coagulation-Solidified Albumin/Hemoglobin Complex In Example 1, it was demonstrated that the denaturation coagulation-solidified plasma carrier adsorbed with undenatured hemoglobin has an antigen-presenting cell-stimulating effect. In this experiment, albumin, which is a typical example of serum protein, and hemoglobin derived from erythrocyte were mixed beforehand, and antigen-presenting cell-stimulating effect of this mixture solidified by denaturation coagulation was examined.
(1) Method for Preparing Samples for Bioassay A marketed biological preparation standard human serum albumin (Kenketsu albumin 25 "Kaketsuken", produced by the Chemo-Sero-Therapeutic Research Institute, henceforth referred to as "25% HSA") was mixed with human hemoglobin (H7379-5G, produced by SIGMA, dissolved and suspended in physiological saline) at the following ratios to prepare liquids, the liquids were solidified by a heat treatment at 110° C. for 5 minutes, and the solidification products were roughly ground with a spatula. A 10% neutral buffered formalin solution (20 mL) was added to the ground products, and they were left at room temperature for 3 days to attain formalin fixation. Each fixed ground product was washed with physiological saline, and then ground for 10 minutes on a widely used tissue-grinding machine (Tissue Lyser II, produced by Qiagen), on which a microtube can be set. The ground fragments were passed through a mesh having a pore diameter of 70 μm, centrifuged with a sufficient volume of physiological saline, sterilized by immersion in ethanol, and then washed again by centrifugation with a sufficient volume of physiological saline. An appropriate volume of physiological saline was added to the fragments and suspend them, so that the volume ratio of the fragments was 25 v/v % after centrifugation at 3,000 rpm for 15 minutes on a desktop centrifuge, to prepare a sample for bioassay "denaturation coagulation-solidified hemoglobin-albumin microparticle suspension". The samples prepared in this manner were those of the following types of different hemoglobin ratios.
Sample 1: 25% HSA 3.0 mL
Sample 2: 25% HSA 2.4 mL+100 mg/mL Hemoglobin 0.6 mL
Sample 3: 25% HSA 1.84 mL+220 mg/mL Hemoglobin 0.909 mL+Physiological saline 0.251 mL
Sample 4: 25% HSA 1.04 mL+220 mg/mL Hemoglobin 1.818 mL+Physiological saline 0.141 mL
Sample 5: 220 mg/mL Hemoglobin 3.0 mL Sample 6: Physiological saline 3.0 mL (TNFα production amount obtained with this sample was used as the blank value)

At the time of the assay culture, each of these samples was added to a well containing 0.5 mL of the 3% medium in a volume of 32 µL per well. Three wells were used for one kind of sample, and average values were used as data.

Figure 2:
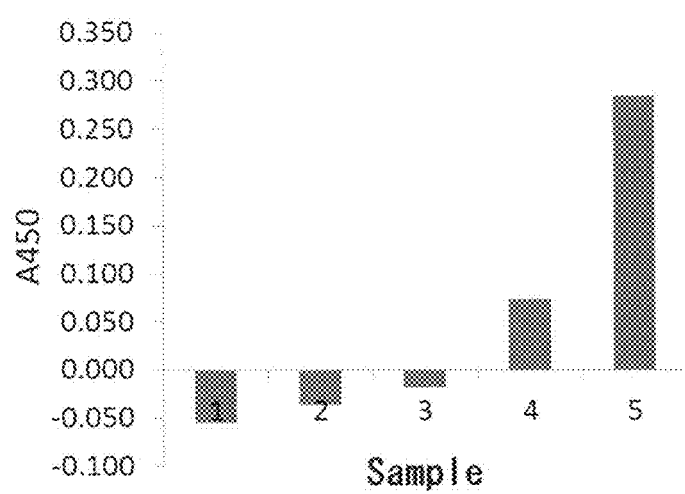
FIG. 2 A graph showing the antigen-presenting cell-stimulating activities of Samples 2 to 5 used in Example 2 (carriers prepared by solidifying a mixture of hemoglobin and albumin by denaturation coagulation, denaturation coagulation-solidified hemoglobin/albumin microparticles (HAMP)).

(2) The method for the bioassay using the antigen-presenting cells and the method for measuring TNFα were performed in the same manners as those performed in Example 1 using SAv-HRP. The results for the TNFα production amount are shown in FIG. 2. The values are those obtained after subtraction of the blank value (Sample 6). These results indicate that with the denaturation coagulation-solidified albumin microparticles (Sample 1) alone, the TNFα production amount is suppressed compared with the original blank value, and with the microparticle Samples 2 to 5 obtained by solidifying albumin and hemoglobin by denaturation solidification, the antigen-presenting cell-stimulating effect increases as the hemoglobin content increases.

(3) Measurement of Endotoxin Content in Samples and Results Thereof

If the samples used in Example 1 and the aforementioned samples for bioassay were contaminated with endotoxins, they might affect the results. Therefore, endotoxin content was measured. For the measurement, Kinect-QCL 192 Test Kit (produced by Lonza), and *E. coli* 055:B5 as standard endotoxin were used, and the measurement method was according to the instructions attached to the kit. As a result, the endotoxin content was below the detection limit (<0.500 EU/mL) for all the samples for bioassay of Example 1 mentioned above, and the samples for bioassay used in this experiment. On the basis of these results, it was judged that endotoxins did not affect the results shown in FIGS. 1 and 2.

In the following examples, the denaturation coagulation-solidified hemoglobin-albumin microparticles (abbreviated as HAMP) containing HSA and hemoglobin at the ratios corresponding to those of "Sample 2" mentioned above was used as a typical example, and they were used after the concentration was adjusted by concentrating them by centrifugation at 3,000 rpm (maximum acceleration was 1580 G) at room temperature for 15 minutes on a desktop centrifuge to precipitate them. The HAMP concentration after the concentration operation is represented in terms of w/v % as the weight ratio of the precipitates, or v/v % as the volume ratio of the precipitates.

Example 3: Role of Peroxidase-Like Activity in Denaturation Coagulation-Solidified Protein Microparticles It is widely known that such a protein as hemoglobin and myoglobin has a strong peroxidase-like activity. Since this activity is exhibited even in a pathological tissue section obtained after formalin fixation and paraffin embedding treatment, if a pathological tissue section contains a large amount of hemoglobin, an undesired staining image may be formed in immunostaining using a peroxidase-labeled antibody. This activity can be eliminated by an aqueous hydrogen peroxide treatment (Non-patent document 26). It is considered that the peroxidase-like activity of HAMP mentioned above is also very strong.

(1) Peroxidase Activity of Sample 2 (Qualitative Test)

Among the samples for bioassays prepared in Example 2, (1), Sample 2 having the lowest hemoglobin ratio was used as a representative example of HAMP. This sample was centrifuged, weight of the precipitates was measured, and then the precipitate content was adjusted to 40 w/v % with physiological saline to prepare a suspension. When 20 µL of this suspension was added to 200 µL of a marketed TMB substrate solution widely used for the color reaction with peroxidase, the colorless TMB substrate solution changed to a deep blue color solution within several seconds. This confirmed that the peroxidase-like activity of HAMP is also very strong.

When a suspension of myoglobin-albumin microparticles (20 µL) prepared in the same manner as that used for Sample 2 except that horse myoglobin was used instead of hemoglobin used for Sample 2 was added to 200 µL of the TMB substrate solution, the colorless TMB substrate solution changed to a deep blue color solution within 1 minute. Therefore, a protein showing a peroxidase-like activity even after solidification by denaturation coagulation can be used like HAMP.

(2) Antigen-Presenting Cell-Stimulating Effect of Sample 5 Subjected to Peroxidase-Like Activity Inactivation Treatment with Aqueous Hydrogen Peroxide (Quantitative Test)

It is widely known that the peroxidase-like activity in a pathological tissue section prepared by formalin fixation and paraffin embedding is eliminated by an aqueous hydrogen peroxide treatment. When an excess amount of aqueous hydrogen peroxide was added to Sample 2 for bioassay used in Example 2, and the sample was left over night, and then repeatedly washed with physiological saline by centrifugation, Sample 2 did not show the coloring reaction of the TMB substrate solution. On the other hand, the peroxidase-like activity of Sample 5 having the highest hemoglobin ratio is strongest among the samples for bioassay used in Example 2, (1), and therefore 1) purified water, or 2) 3% aqueous hydrogen peroxide (900 µL) was added to 150 µL of Sample 5, and they were stirred overnight at room temperature. The mixture was centrifuged at 4° C. and 12,000 rpm (maximum acceleration was 11,000 G) for 5 minutes on a cooled microcentrifuge to obtain precipitates, the precipitates were washed with a sufficient volume of physiological saline by centrifugation, then 112.5 µL of physiological saline was added to the precipitates to suspend them to obtain a sample for bioassay 1) Hemoglobin-MP, and 2) $H_2O_2$-Hemoglobin-MP, respectively. The bioassay method using the antigen-presenting cells and the measurement method for TNFα were the same as those used in Example 1.

Figure 3:
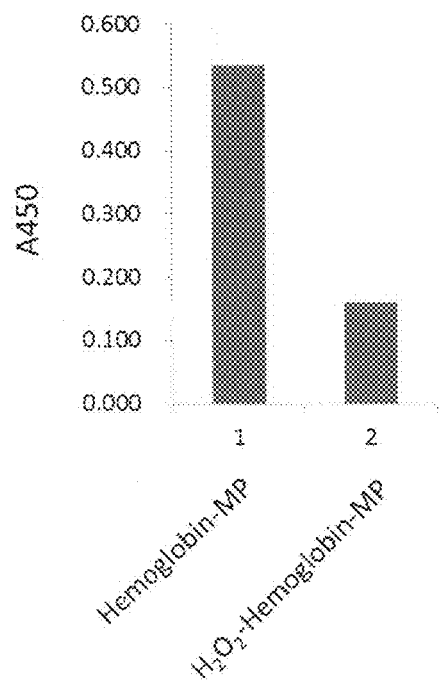
FIG. 3 A graph showing that the peroxidase-like activity originating in hemoglobin of HAMP is participating in the antigen-presenting cell-stimulating action as shown in Example 3.

The results for the TNFα production amount are shown in FIG. 3. The values obtained after subtraction of the blank value (physiological saline was used as the sample for bioassay) are shown. These results show that when the peroxidase-like activity is eliminated by an aqueous hydrogen peroxide treatment, the TNFα production is evidently suppressed, i.e., the peroxidase-like activity in the denaturation coagulation-solidified hemoglobin fragments contributes to the antigen-presenting cell-stimulating effect.

Example 4: Adsorption of Purified Tuberculin to HAMP

Purified tuberculin is a typical immunostimulating substance that induces the type IV allergic response (namely, cell-mediated immunoreaction). It is known that, although the purified tuberculin itself is essentially a stable substance, when it is dissolved, it is adsorbed on an internal surface of glass bottle, and easily causes apparent inactivation, and that such adsorption can be prevented with human serum albumin (Non-patent document 16). Therefore, it was examined whether HAMP adsorbs purified tuberculin.

(1) Method for Quantifying Purified Tuberculin

There was obtained the HuCAL-Fab antibody (GeneFrontier Corporation, Kashiwa-shi, Chiba) directed to DnaK, which is one of the proteins derived from *Mycobacterium tuberculosis* (Non-patent document 24), and contained in purified tuberculin for general diagnosis (PPD) (1 µg/vial, Japan BCG Laboratory). By using this antibody as the primary antibody, and the antibody #109-035-097 of Jackson Immuno Research as the secondary antibody, an ELISA-based quantification method for purified tuberculin was established. The method was the usual ELISA quantification method well known to those skilled in the art except that the purified tuberculin (PPD) was used as an antigen, and the primary antibody, and secondary antibody mentioned above were used. For the final color reaction, the widely used TMB substrate solution for horseradish peroxidase and the reaction stop solution used in Example 1, (3) were used, and the results are indicated as values of A450. In this experiment, physiological saline was used for blank. The A450 value obtained after subtraction of the blank value for a concentration of the aforementioned PPD of 1.25 µg/mL (volume for the ELISA reaction was 200 µL per well of 96-well microplate for ELISA) was 0.063, and it was within the range for which quantification is possible.

(2) Adsorption Reaction to HAMP

HAMP (suspended in an appropriate volume of physiological saline so that volume ratio of the microparticles obtained after centrifugation at 3,000 rpm (maximum acceleration was 1580 G) for 15 minutes on a desktop centrifugation machine became 40 v/v %) was put into a plastic microtube in such a volume that the final concentration should become 20 v/v %, PPD mentioned above was added at a concentration of 1.25 µg/mL, and the mixture was stirred at room temperature. The stirring time was 30 minutes to 6 hours. After the stirring, the mixture was centrifuged at 4° C. and 12,000 rpm (maximum acceleration was 11,000 G) for 5 minutes on a high-speed microcentrifugation machine to obtain a supernatant. By using 150 µL of this supernatant, the amount of PPD in the supernatant was measured by the aforementioned ELISA quantification method (using physiological saline as the blank).

(3) Results

Figure 4:
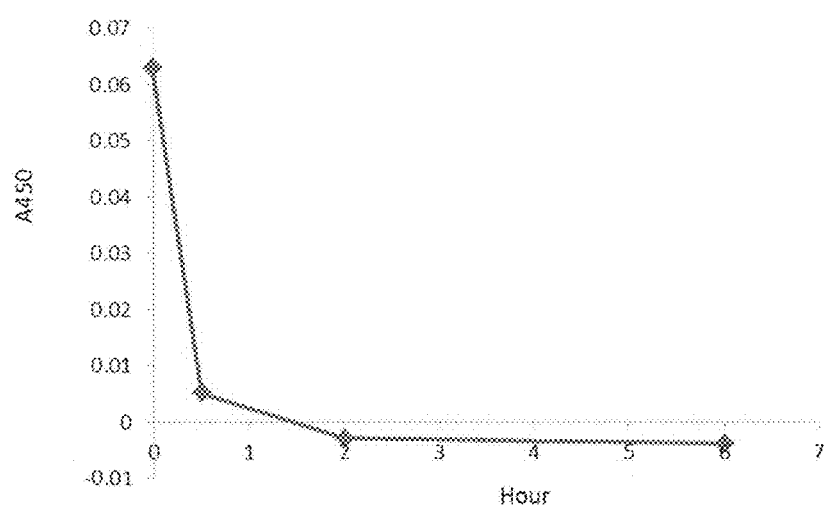
FIG. 4 A graph showing ability of HAMP to adsorb purified tuberculin (PPD).

The amounts of PPD remaining in the supernatant are shown in FIG. 4 as A450 values obtained after subtraction of the blank value. These results show that 92% of PPD adsorbed to HAMP after stirring at room temperature for 30 minutes. It is considered that, if the stirring was performed for 2 hours or longer, substantially whole amount of PPD adsorbed on HAMP (although there was some measurement error that the minimum value of A450 was −0.004). These results also show that a heterogeneous protein that can serve as an antigen can also adsorb to HAMP.

Example 5: Antigen-Presenting Cell-Stimulating Effect of PPD and Cytokine Adsorbed on HAMP As shown in Example 4, HAMP has strong adsorption power for PPD. Therefore, there were examined antigen-presenting cell-stimulating activity of such adsorbed PPD, and whether cytokine-adsorbed HAMP on which a cytokine that exhibits an important action in the living body is adsorbed shows antigen-presenting cell-stimulating activity.

(1) Adsorption operation

To a 50-mL centrifugation tube, HAMP precipitates and PPD suspended in physiological saline were added at concentrations of 25 v/v % and 286 ng/mL, respectively, and the mixture was stirred at room temperature for 2 hours. The resulting mixture was used as PPD-HAMP suspension.

Human granulocyte-macrophage colony-stimulating factor (hGM-CSF, Leukine (sargramostim), produced by Sanofi-Aventis U.S. LLC) was dissolved in water at a concentration of 100 µg/mL. This solution (100 µL) and HAMP (25 w/v %, 200 µL, prepared on the basis of weight of denaturation coagulation-solidified hemoglobin-albumin microparticle precipitates) were combined, and the mixture was stirred at room temperature for 2 hours. After the stirring, the mixture was centrifuged at 4° C. and 12,000 rpm (maximum acceleration was 11,000 G) for 5 minutes on a high-speed microcentrifugation machine to obtain precipitates. Centrifugation washing by suspending the precipitates in physiological saline (750 µL), and centrifuging the suspension in the same manner as described above was repeated 3 times in total, and physiological saline (150 µL) was added to the finally obtained precipitates to prepare a hGM-CSF-HAMP suspension.

In the case of human interleukin-2 (hIL-2), physiological saline (625 µL) was put into a vial of Imunace Injection 35 (containing 350,000 units of Teceleukin (produced by genetic recombination technique, substantially hIL-2) per vial, Shionogi Pharmaceuticals) to dissolve it, the solution (50 µL) and HAMP (200 µL) were mixed, and the mixture was stirred at room temperature for 2 hours. Then, the same operation as that used for hGM-CSF mentioned above was performed to prepare a hIL-2-HAMP suspension. In the case of human interferon γ (hIFNg, Wako Pure Chemical Industries), a 50 ng/mL solution thereof in physiological saline was prepared, the solution was mixed with HAMP (200 µL), and the mixture was stirred at room temperature for 2 hours. Then, the same operation as that used for hGM-CSF mentioned above was performed to prepare a hIFNg-HAMP suspension.

(2) The bioassay method using antigen-presenting cells and the method for measuring TNFα were the same as those used in Example 1. In the measurement of TNFα, SAv-HRP was used. In this experiment, each of the following solutions or suspensions was added per one well as a sample for bioassay.

Sample 1: Physiological saline, 32 µL (TNFα production amount obtained with this sample was used as the blank value)

Sample 2: PPD solution obtained by dissolving purified tuberculin for general diagnosis (PPD) for one person (0.25 µg/vial, Japan BCG Laboratory) in 1.2 mL of physiological saline, 32 µL Sample 3: HAMP suspension, 32 µL Sample 4: PPD-HAMP (HAMP adsorbed with PPD) suspension, 32 µL Sample 5: hGM-CSF-HAMP (HAMP adsorbed with hGM-CSF) suspension, 32 µL Sample 6: hIL-2-HAMP (HAMP adsorbed with hIL-2) suspension, 32 µL Sample 7: hIFNg-HAMP (HAMP adsorbed with hIFNg) suspension, 32 µL Three wells were used for one kind of sample. The culture medium collected after assay culture for 22 hours was diluted with fresh 3% medium to 1/2 concentration, and used in the measurement of TNFα based on ELISA.

(3) Results

Figure 5:
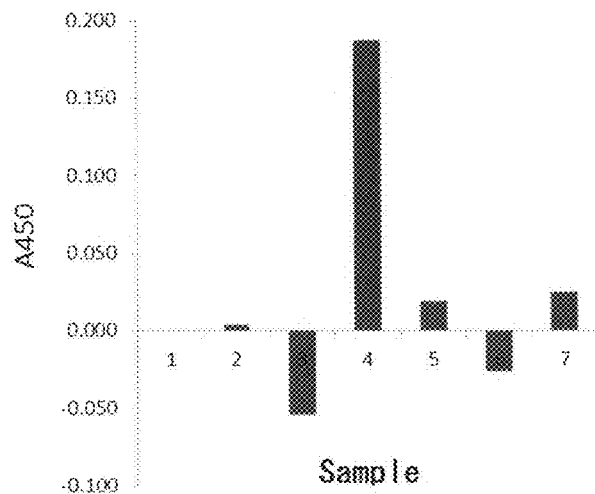
FIG. 5 A graph showing the action of HAMP adsorbed with an immunostimulating substance such as PPD or hGM-CSF for stimulating antigen-presenting cells.

The average values of the A450 values for the three wells obtained after subtraction of the blank value are shown in FIG. 5. In the case of Sample 4, it contained PPD in a twice larger amount in the added volume of 32 µL compared with Sample 2, and therefore the half of the actually measured A450 value 0.374, i.e., 0.187, is used in the graph.

According to these results, PPD in the form of solution (Sample 2) gave the result of the same level as that of physiological saline (Sample 1) used as the blank (A450 value was 0.004, which is in the range of measurement error similarly to that observed in Example 3), and did not show the antigen-presenting cell-stimulating effect. Further, while HAMP alone (Sample 3) provided suppressed production amount of TNFα compared with the blank value that should be normally obtained, similarly to Example 2, PPD-HAMP (Sample 4), which is HAMP adsorbed with PPD, showed the stimulating effect. Therefore, it became clear that antigen-presenting cells can be more strongly activated with PPD adsorbed and fixed on HAMP which are solidified fragments of the soluble PPD.

In the cases of hGM-CSF-HAMP (Sample 5, A450 value was 0.019), and hIFNg-HAMP (Sample 7, A450 value was 0.025), on which cytokine was adsorbed, production of TNFα was definitely observed, although the levels thereof were low. However, hIL-2-HAMP (Sample 6) did not show the effect at a level higher than that observed for physiological saline (Sample 1) used as the blank.

As described in Example 1, (2) mentioned above, when differentiation of the THP-1 cells into antigen-presenting cells is induced, it is necessary to add a very small amount of IFNg to the culture medium as a trigger for the TNFα production. It is considered that, in the case of HAMP alone, HAMP adsorbed such a very small amount of IFNg in the culture medium, and therefore Samples 1 and 2 of Example 2, and Samples 3 and 6 of this example gave negative A450 values.

Example 6: Antigen-Presenting Cell-Stimulating Effect of HAMP Adsorbed with BCG Bacteria Extract The results of Example 5 revealed that the soluble PPD adsorbed on HAMP can more strongly activate antigen-presenting cells, and therefore it was examined whether such an effect can also be expected for other immunostimulating substances. In this experiment, BCG bacteria extract (BCGext) containing various low molecules was used.

(1) Method for Preparing BCGext

Content of one ampoule of dry BCG vaccine ampoule (containing 12 mg, Japan BCG Laboratory) was autoclaved at 110° C. for 5 minutes, 1 ml of ethanol was added, the mixture was stirred for 6 hours or more, then the resulting suspension was collected and added to content of another one ampoule of the dry BCG preparation, the mixture was sufficiently stirred again, and centrifuged at 12,000 rpm (maximum acceleration was 11,000 G) for 5 minutes on a high-speed microcentrifugation machine, and the supernatant was collected as BCGext.

(2) Adsorption of BCGext to HAMP

To HAMP (40 w/v %), the same volume of BCGext diluted with ethanol to 1/5 concentration was added, and the mixture was stirred overnight at room temperature. This mixture was washed with a sufficient volume of physiological saline by centrifugation, and suspended at the original concentration of HAMP (40 w/v %). The suspension was diluted 5.65 times with the 3% medium to prepare a sample HAMP-BCGext.

(3) The bioassay method using antigen-presenting cells and the method for measuring TNFα were the same as those used in Example 1, and SAv-HRP was used in the measurement of TNFα.

In this experiment, each of the followings was added per one well as a sample for bioassay.

Sample 1: Physiological saline, 30 μL (TNFα production amount obtained with this sample was used as the blank value)

Sample 2: HAMP (40 w/v %) diluted 5.65 times with physiological saline, 30 μL (final concentration at the time of assay culture was 0.4 w/v %)

Sample 3: BCGext diluted 28.3 times with the 3% medium, 30 μL (final concentration at the time of assay culture was 0.2 v/v %)

Sample 4: HAMP-BCGext, 30 μL (final concentration of HAMP at the time of assay culture was 0.4 w/v %, a sample that should give a final concentration of 0.18 v/v % if all the originally contained BCGext was adsorbed to HAMP)

(4) Results

Figure 6:
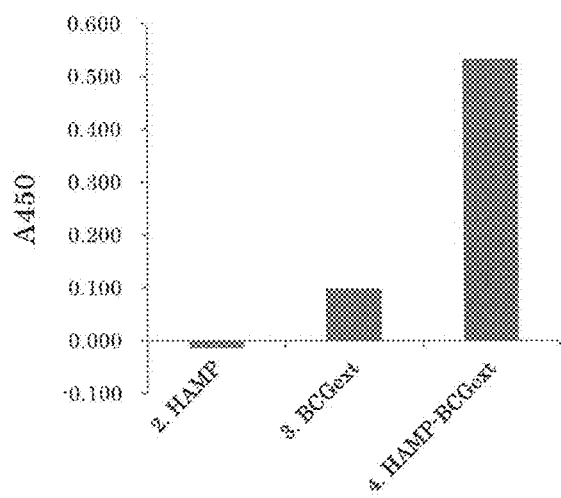
FIG. 6 A graph showing the action of HAMP adsorbed with a BCG bacteria extract (BCGext) for stimulating antigen-presenting cells.

The results are shown in FIG. 6. These results indicate that the antigen-presenting cells can be more strongly stimulated with BCGext adsorbed on HAMP compared with BCGext per se. That is, if a soluble immunostimulating substance, not limited to PPD, can be adsorbed on HAMP, it becomes a more potent immunostimulant, and therefore it can be seen that HAMP is an effective carrier of an immunostimulating substance.

(5) HAMP-BCGext was prepared in the same manner as described in the preceding section (provided that HAMP was not diluted 5.65 times with the 3% medium, but suspended in the 3% medium at the original HAMP concentration (40 w/v %), which is defined as 1/1 concentration), suspensions were prepared by diluting it with the culture medium for assay to 1/50 to 1/800 concentrations, and used in the bioassay using antigen-presenting cells. At the time of the quantification of the amount of the produced TNFα in the collected supernatant, the standard TNF attached to the measurement kit based on the ELISA method (OptEIA Set Human TNF produced by BD Biosciences, Cat. No. 555212) was used, and the results were represented as amounts of TNF. At the time of the quantification of the amount of the produced GM-CSF in the collected supernatant (this GM-CSF was hGM-CSF, since the THP-1 cells were derived from human), the standard GM-CSF attached to the measurement kit based on the ELISA method (GM-CSF ELISA Kit produced by Thermo Scientific, Cat. No. EHGMCSF), and the results were represented as amounts of GM-CSF.

(6) Results

Figure 7:
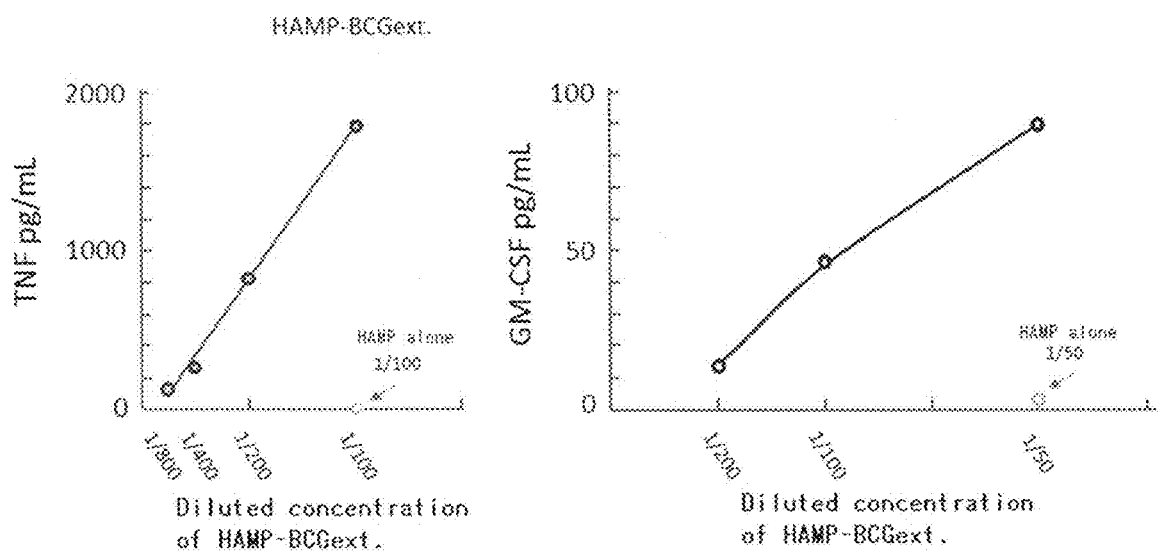
FIG. 7 Graphs showing that GM-CSF is produced simultaneously with TNFα (indicated as TNF in the graphs) from the antigen-presenting cells stimulated with HAMP adsorbed with BCG bacteria extract (BCGext).

The results are shown in FIG. 7. These results revealed that hGM-CSF was simultaneously produced in an amount corresponding to about 1/40 of the amount of TNFα.

As observed for Sample 5 in Example 5, hGM-CSF can directly adsorb to HAMP, and the adsorbed hGM-CSF can stimulate and activate antigen-presenting cells. Therefore, it was revealed that there operates an autocrine mechanism that stimulus given by HAMP carrying BCGext triggers production of hGM-CSF by antigen-presenting cells, and it also acts on the antigen-presenting cells themselves, and activates them. It is well known to those skilled in the art that there is also a paracrine action that the produced hGM-CSF not only acts on the antigen-presenting cells that produced it themselves, but also can act on neighboring antigen-presenting cells and activate them, even though the antigen-presenting cells present a different kind of antigen molecule. Accordingly, with the immunostimulant of the present invention, hGM-CSF secreted from the stimulated antigen-presenting cells can enhance general immunoreactions through the action thereof on neighboring antigen-presenting cells, and therefore it can be used as BRM without administering any other specific antigens.

Example 7: Adsorption of Antibody to HAMP (1)

It is known that antibodies may have an immunostimulating action depending on the type thereof. On the basis of the results obtained in the preceding examples, it was presumed that HAMP has an ability to adsorb various kinds of molecules. Therefore, it was examined whether it also adsorbs antibodies.

(1) Adsorption Operation

A marketed goat anti-mouse IgG (H+L) antibody (labeled with horseradish peroxidase, produced by Promega, Cat. No. W4021) was diluted to 1/25,000 concentration with Dulbecco's Ca+ and Mg$^+$-free phosphate buffer (PBS(-)). The diluted antibody (20 µL) was taken and added to a suspension containing HAMP (60 µL) and physiological saline (920 µL), and the mixture was stirred at room temperature for 0 to 60 minutes. After the stirring, the mixture was immediately centrifuged at 4° C. and 12,000 rpm (maximum acceleration was 11,000 G) for 5-minute on a cooled high-speed microcentrifuge, and the peroxidase activity of the antibody remained in the supernatant (100 µL) was measured. The peroxidase activity was represented in terms of A450 value obtained by using the color reaction observed with the TMB substrate solution attached to the TNFα measurement kit used in the method for measuring TNFα mentioned in Example 1, (3).

(2) Results

Figure 8:
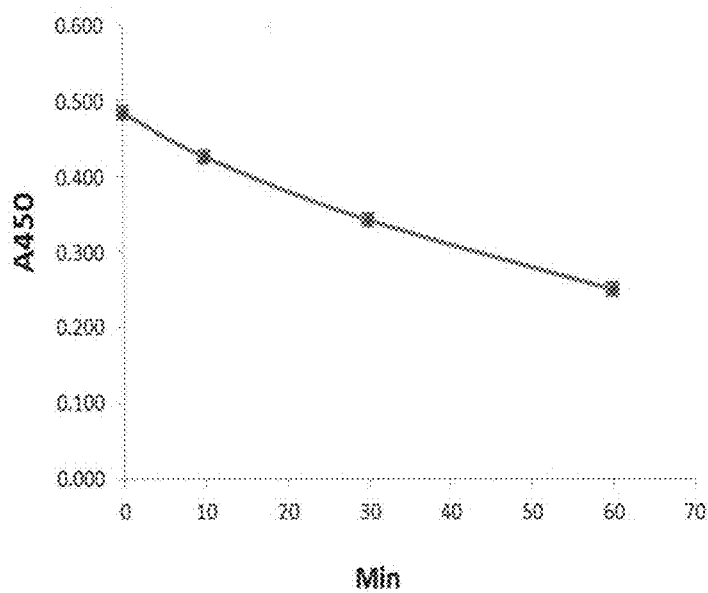
FIG. 8 A graph showing the adsorption ability of HAMP to antibodies.

As shown in FIG. 8, the peroxidase activity in the supernatant decreased in a mixing time-dependent manner. Since it is known that when HAMP is not added to the goat anti-mouse IgG (H+L) antibody, diluted solution of the antibody does not show change of the activity in about 1 hour, and therefore this decrease indicates that the antibody gradually adsorbs to HAMP precipitates over time. This result also shows that when it is desired to use a goat antibody as an antigen protein, it can be used as a solidified antigen comprising the antibody adsorbed on HAMP, not as an antibody solution.

Example 8: Adsorption of Antibody to HAMP (2)

It was examined whether such adsorption of antibody similarly occurs with another kind of antibody.

(1) Adsorption Operation

A marketed rabbit anti-goat IgG (total molecule) antibody (labeled with alkaline phosphatase, A4187, produced by Sigma-Aldrich) was diluted 1,000 times with PBS (-), and used as the primary antibody. This primary antibody (100 µL) was taken, and added to a suspension containing HAMP (60 µL) and physiological saline (840 µL), and the mixture was stirred at room temperature for 0 to 60 minutes. After the stirring, the mixture was immediately centrifuged at 4° C. and 12,000 rpm (maximum acceleration was 11,000 G) for 5 minutes on a cooled high-speed microcentrifuge, and the resulting precipitates were washed by centrifugation with a sufficient volume of physiological saline. The washed precipitates were suspended in physiological saline (100 µL), and to the half volume of the suspension, a buffer for alkaline phosphatase (TRACP & ALP Assay Kit produced by Takara Bio, Code No. MK301) and 190 µL of the reaction substrate solution of this kit were added according to the instruction. The mixture was stirred at room temperature for 10 minutes, and 30 µL of a reaction stop solution (0.5N NaOH) was added. Then, the reaction mixture was centrifuged at 4° C. and 12,000 rpm (maximum acceleration was 11,000 G) for 5 minutes on a cooled high-speed microcentrifuge, 200 µL of the supernatant was taken, and the absorbance thereof was measured at 405 nm.

(2) Results

Figure 9:
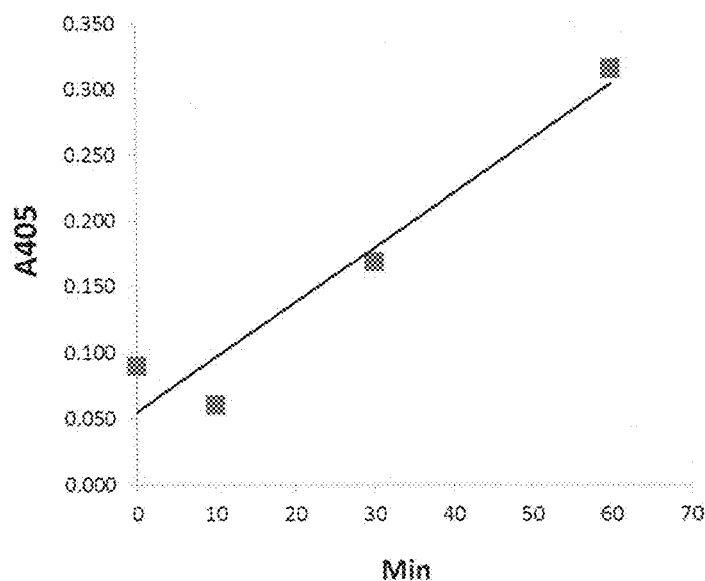
FIG. 9 A graph showing the adsorption ability of HAMP to antibodies.

As shown in FIG. 9, the alkaline phosphatase activity in the precipitates increased as the length of the time of the stirring with the primary antibody increased. That is, it was demonstrated that the rabbit anti-goat IgG (total molecules) antibody also adsorbs to HAMP. Therefore, it can be seen from the results of Examples 7 and 8 that HAMP adsorbed with antibody can also be an effective composition of an immunostimulant. When HAMP adsorbed with an antibody is used as an immunostimulant, individual antibodies are not immediately dissolved and diffused at the topical administration site, and therefore it is clear from the results that there can be realized an effective antibody application method by which the application of the antibody can be limited to a topical administration site.

Example 9: Safety of PPD-HAMP

In Example 5, the antigen-presenting cell-stimulating effect of cytokine absorbed to HAMP was observed for hGM-CSF and hIFNg, but was not observed for hIL-2. It is known that all of these cytokines easily bind to heparin, and hIL-2, in particular, shows the activity thereof in a state that it binds to heparin (Non-patent document 25). Therefore, there were prepared microparticles comprising a solidified carrier of a type other than HAMP, albumin-heparin coacervate precipitates (in the form of microparticles, Patent document 4, Patent document 4 describes albumin-heparin coacervate precipitates containing PPD, but in this example, albumin-heparin coacervate precipitates not containing PPD (designated as nega-TuMP) adsorbed with hIL-2 (hIL-2-MP) was used), and it was examined whether they show any antigen-presenting cell-stimulating effect.

The method for preparing microparticle tuberculin described in Patent document 4, Example 1, the section of Materials and methods, 1. Immunoadjuvant (the product of this method corresponds to nega-TuMP containing PPD) was performed just without adding PPD to prepare nega-TuMP. The suspension of nega-TuMP in the form of microparticles (1 mL) contained 625 units of heparin and 12.5 mg of human serum albumin. Imunace Injection 35 (Shionogi Pharmaceuticals) was dissolved in 625 µL of water for injection, 50 µL of this solution (28,000 units of hIL-2) was taken, and mixed with 100 µL of the nega-TuMP suspension, and the mixture was stirred overnight at room temperature to allow adsorption of hIL-2 to nega-TuMP in the form of microparticles. The resultant was used as the sample for bioassay using antigen-presenting cells, hIL-2-MP, in the same manner as in Example 1. The control for the comparison in this case was the same amount of nega-TuMP alone. The method of the bioassay using antigen-presenting cells and the method for measuring TNFα used in this experiment were the same as those used for the experiment performed by using SAv-HRP in Example 1. As a result, the A450 values, which are proportional to the amount of TNFα in the finally collected culture medium of the antigen-presenting cells, were −0.016 for nega-TuMP alone, and −0.006 for hIL-2-MP.

Both of these samples did not have the antigen-presenting cell-stimulating property, and they rather slightly decreased the TNFα production. It is considered that the above result was obtained because nega-TuMP has a property of adsorbing IFNg, and therefore it decreased the concentration of a very small amount of IFNg for triggering added to the culture medium in the both cases including the case of hIL-2-MP. However, at least nega-TuMP itself does not directly activate antigen-presenting cells.

On the basis of the above results, the safety was examined by using a mixture of nega-TuMP and PPD-HAMP as a sample, and weight change and organ weight change observed in mice at the growth stage administered with the sample as indexes, which are basic indexes of toxicity test.

(1) Method

Fourteen 5 weeks old C3H/HeN (male) mice were divided into two groups, and 50 μL of physiological saline, and 50 μL of a suspension containing PPD-HAMP (19.1 v/v % as the amount of precipitates obtained by centrifugation at 3,000 rpm (maximum acceleration was 1,580 G) for 15 minutes) and a nega-TuMP suspension (8.7% as volume ratio) were intracutaneously injected to each mouse of the control group and the treatment group, respectively, at the tale base part thereof once a week, 3 times in total. From next week, the sample was also subcutaneously injected at the femoral part once a week, 6 times in total, and body weight was measured. Further, 7 days after the final injection, weights of the spleen, kidney, and liver of each mouse were measured.

(2) Results

Figure 10:
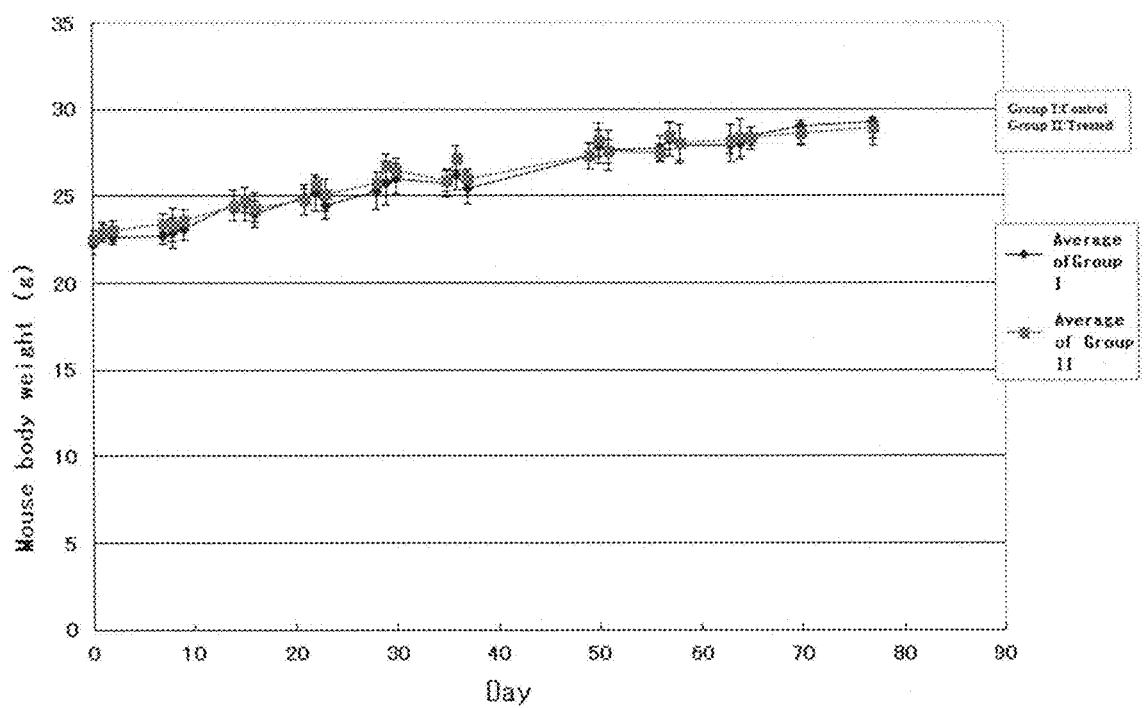
FIG. 10 A graph showing safety of HAMP made to carry PPD (mouse weight change).
Figure 11:
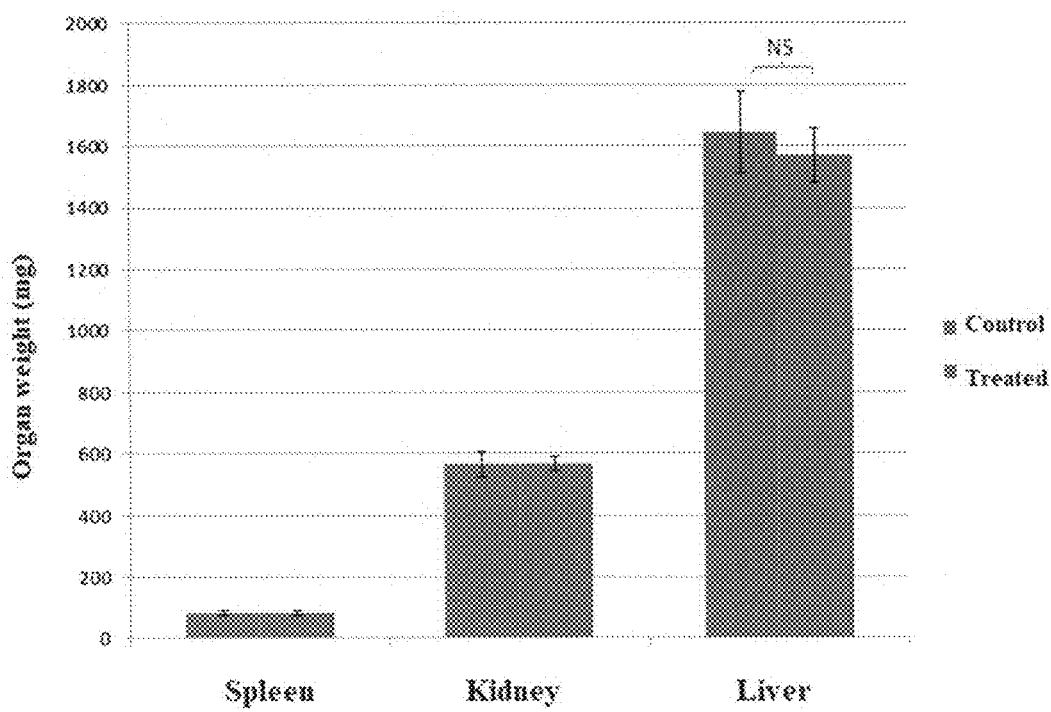
FIG. 11 A graph showing safety of HAMP made to carry PPD (organ weight change). NS (not significant) means that any statistically significant difference was not observed.

The weight change of the mice is shown in FIG. 10, and organ weights are shown in FIG. 11. These results indicate that the suspension as a mixture of PPD-HAMP and nega-TuMP does not have strong toxicity that gives weight loss to mice, and it does not have such a serious problem concerning safety well known to those skilled in the art as that observed when the Freund's complete adjuvant (FCA) is administered.

Example 10: Antitumor Effect of Cancer Vaccine Comprising Mixture of Cancer Antigen and Immunostimulant (1)

As shown in Example 4, HAMP can quickly adsorb PPD, and make soluble PPD insoluble, and as shown in Example 5, they can stimulate antigen-presenting cells. Therefore, PPD-HAMP is estimated to be an effective immunoadjuvant. Further, as shown in Example 5, HAMP can adsorb a cytokine. Further, it is well known to those skilled in the art that cytokines well adsorb to heparin, and cytokines also well adsorb to nega-TuMP produced by coacervation of heparin and albumin. Therefore, nega-TuMP mixed and adsorbed with a cytokine was added to PPD-HAMP, and the effect of the mixture as an immunoadjuvant was examined.

(1) Methods (1-1) Production of Nega-TuMP Adsorbed with Cytokine

Mouse GM-CSF (100 μg, produced by Miltenyi Biotec, premium grade) was dissolved in purified water (1 mL). This solution (50 μL) was mixed with the nega-TuMP suspension (100 μL), and the mixture was stirred overnight at room temperature to allow adsorption and thereby prepare mGM-CSF-MP. Separately, Imunace Injection 35 (Shionogi Pharmaceuticals) was dissolved in water for injection (625 μL), 50 μL of this solution was taken and mixed with 100 μL of the nega-TuMP suspension, and the mixture was stirred overnight at room temperature to prepare hIL-2-MP.

(1-2) Liquid Compositions of Antigen and Immunoadjuvant

Ovalbumin (1.12 mg, produced by Calbiochem, catalog number 32467, abbreviated as OVA) was dissolved in physiological saline (1 mL), and by using this solution as an antigen stock solution, liquid compositions containing cytokine-adsorbed (or non-adsorbed) nega-TuMP as an immunoadjuvant corresponding to the G1 to G4 groups of mice were prepared at the liquid volume ratios shown in the following table.

TABLE 2

| | Group of mouse | | | |
|---|---|---|---|---|
| | G1 | G2 | G3 | G4 |
| Physiological saline | 450 μL | 50 μL | 50 μL | — |
| PPD-HAMP suspension | — | 350 μL | 350 μL | 350 μL |
| nega-TuMP suspension | — | 50 μL | — | — |
| mGM-CSF-MP | — | — | 50 μL | 50 μL |
| hIL-2-MP | — | — | — | 50 μL |
| OVA stock solution (added only on day 0, and on the other occasions, physiological saline was added instead) | 250 μL | 250 μL | 250 μL | 250 μL |
| Total composition volume | 700 μL | 700 μL | 700 μL | 700 μL |

(1-3) Schedules of Administration to Mice

Each of the liquid compositions mentioned in the above table was intracutaneously injected to 6 weeks old C57BL/6 mice (female, purchased from Clea Japan) in a volume of 50 μL per animal. Each group consisted of 10 mice. The day on which the injection was started was defined to be day 0. The injection in a volume of 50 μL used on this day 0 contained the OVA stock solution. Thereafter, each of the liquid compositions not containing OVA mentioned in the above table was further intracutaneously injected to mice of each group in a volume of 50 μL per animal on days 4, 11, 18, 25, and 32 (5 times in total).

(1-4) Challenge to mice with E.G7-OVA tumor cells

Mouse lymphoma cell line E.G7-OVA cells expressing OVA protein fragments as tumor antigen were obtained from the American Type Culture Collection, and cultured in a conventional manner. The cells were washed with serum-free MEM culture medium, further cultured in the serum-free MEM culture medium for 2 hours, and then washed with serum-free MEM culture medium again. These cells (500,000 cells) were suspended in physiological saline (0.1 mL), the suspension was subcutaneously injected to each mouse mentioned in the paragraph (1-3) at the right lower extremity on day 15 as challenge with tumor cells, and thereafter, the volume of the increasing tumor was measured in a conventional manner. When there was a mouse that survived even after the tumor volume reached 5,000 mm$^3$, the measurement was terminated, and the mouse was euthanized.

(2) Results

Figure 12:
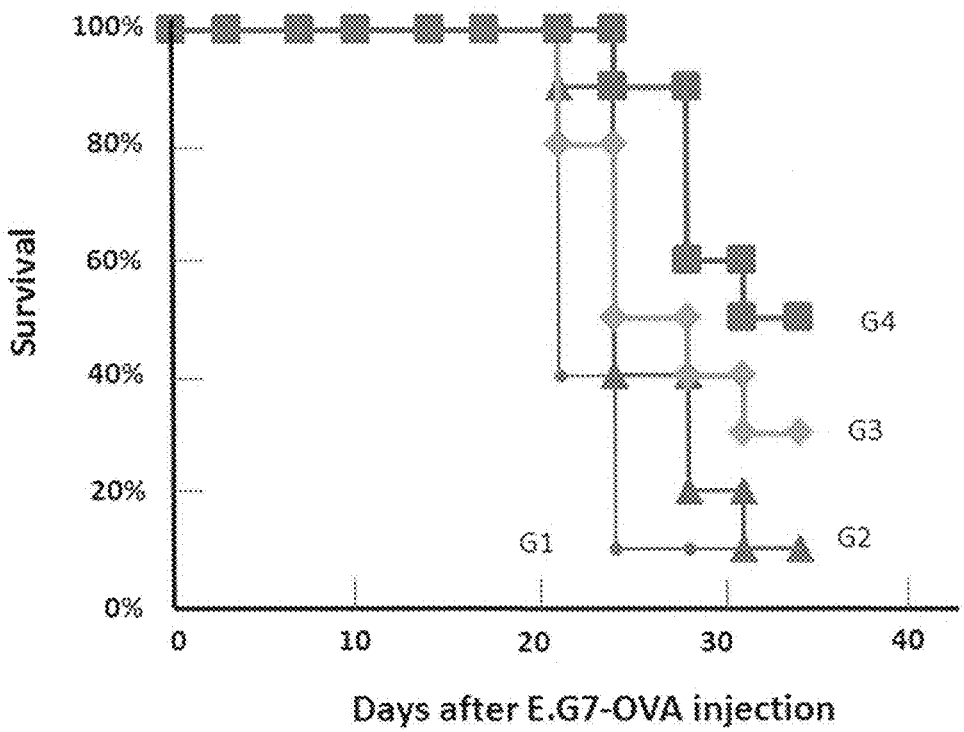
FIG. 12 A graph showing antitumor effect of a cancer vaccine comprising a mixture of a cancer antigen and an immunostimulant.

The results are shown in FIG. 12. The medians of the survival time of the mice after the challenge with E.G7-OVA tumor cells were 21 days for the G1 (control) group (corresponding to day 36 from the day on which the injection of liquid composition was started), 24 days for the G2 (PPD-HAMP-nega-TuMP) group, 26 days for the G3 (PPD-HAMP-mGM-CSF-MP) group, and 31 days or longer for the G4 (PPD-HAMP-mGM-CSF-MP-hIL-2-MP) group. The ratios of the mice that still survived at the end of the 31st day after the challenge were 1/10 for the G1 group, and 5/10 for the G4 group. According to the results of a test for difference of population rate performed between these two groups (chi square test), the two-sided p value was 0.051, and there was observed a strong tendency that life-prolonging effect was observed in the G4 group. Although the other G2 group and G3 group did not show any statistically significant difference with respect to the G1 group, the median survival times of these groups were prolonged compared with the G1 group, and therefore there was observed a tendency that life-prolonging effect was observed in these groups.

Example 11: Antitumor Effect of Cancer Vaccine Comprising Mixture of Cancer Antigen and Immunostimulant (2)

The antigen used in Example 10 was ovalbumin, and although it is widely used as a typical model antigen in immunology, it is not a tumor antigen contained in naturally occurred tumor cells. Therefore, in this example, the immunoadjuvant effect of the PPD-HAMP suspension containing cytokine-adsorbed nega-TuMP as an additive was examined for challenge with living lung cancer cells, where lysate of the same mouse lung cancer cells was used as the tumor antigen.

(1) Methods (1-1) Liquid Compositions of Antigen and Immunoadjuvant

The method for preparing cytokine-adsorbed nega-TuMP suspension was the same as that used in Example 10, paragraph (1-1). The mouse lung cancer cells, LLC cells (obtained from the Institute of Physical and Chemical Research, RIKEN Bioresource Center, cell number RCB0558), were cultured for proliferation in a conventional manner, then cultured under serum-free conditions for 2 hours, and sufficiently washed with PBS(−), and then the cells were separated by a conventional EDTA treatment, and suspended in PBS(−). The cell density of the suspension was adjusted to $2 \times 10^7$ cells/mL, and then the suspension was repeatedly frozen and thawed to prepare a lysate. The lysate was stained with a 3% trypan blue solution to confirm that there was no surviving LLC cell. By using this lysate as the tumor antigen, liquid compositions containing cytokine-adsorbed nega-TuMP (mGM-CSF-MP and hIL-2-MP) as an immunoadjuvant were prepared in the liquid volume ratios shown in the following table so as to correspond to the groups of mice. In this experiment, nega-TuMP itself was not added to the PPD-HAMP suspension.

TABLE 3

| | Group of mouse | | |
|---|---|---|---|
| | Saline | PPD-HAMP | mGM-CSF-hIL-2-PPD-HAMP |
| Physiological saline | 900 μL | 300 μL | — |
| PPD-HAMP suspension | — | 600 μL | 600 μL |
| mGM-CSF-MP | — | — | 150 μL |
| hIL-2-MP | — | — | 150 μL |
| LLC cell lysate (added only on day 0, and on the other occasions, physiological saline was added instead) | 300 μL | 300 μL | 300 μL |
| Total composition volume | 1.2 mL | 1.2 mL | 1.2 mL |

(1-2) Schedules of Administration to Mice

Each of the liquid compositions mentioned in the above table was subcutaneously injected to 6 weeks old C57BL/6 mice (female, purchased from Clea Japan) on their back in a volume of 0.1 mL per animal. Each mouse group consisted of 10 mice, provided that the mGM-CSF-hIL-2-PPD-HAMP group consisted of 8 mice. The day on which the injection was started was defined to be day 0. The injection in a volume of 0.1 mL used on this day contained the LLC cell lysate. Thereafter, each of the liquid compositions not containing LLC cell lysate mentioned in the above table was further subcutaneously injected to mice of each group in a volume of 0.1 mL per animal on days 4, 10, 18, 25, 32, 39, and 46.

(1-3) Challenge to Mice with LLC Cells

Live LLC cells, which are of the original line used for the production of the aforementioned lysate, were suspended in serum-free MEM culture medium (0.1 mL), $1 \times 10^4$ of the cells were subcutaneously injected to each mouse at the right lower extremity on day 15 as challenge with tumor cells, and thereafter, the day on which formation of tumor mass was found by palpation for the first time was recorded. The period after the challenge and up to this day is the tumor-free period.

(2) Results

Figure 13:
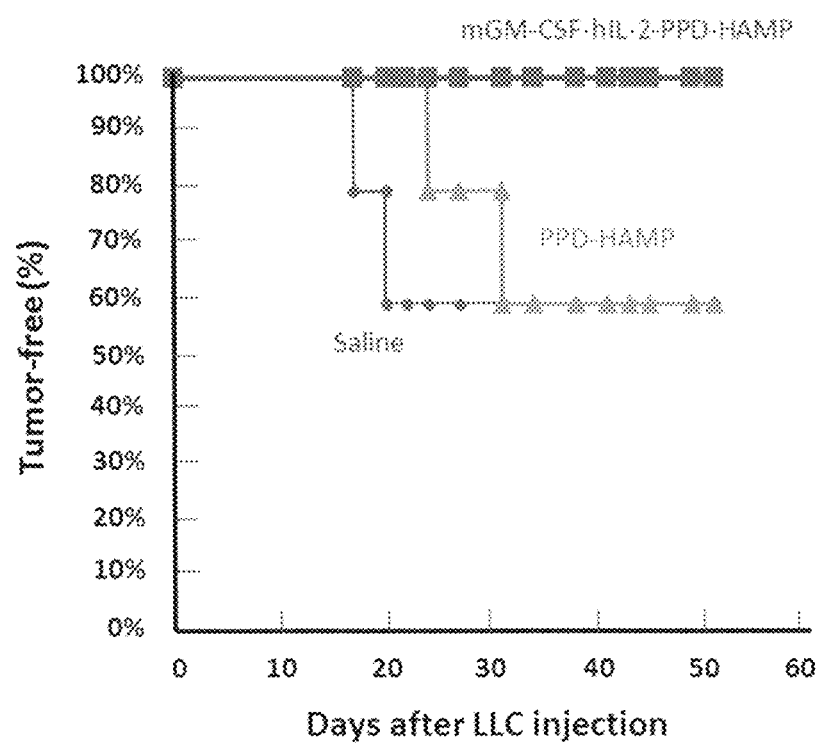
FIG. 13 A graph showing antitumor effect of a cancer vaccine comprising a mixture of a cancer antigen and an immunostimulant.

After the challenge with the LLC cells, observation was continued up to the 53rd day. As a result, the mice remained to be tumor-free in the both groups were as shown in FIG. 13. While generation of tumor mass was observed fro+m the 17th day from the challenge with the tumor cells in the control (saline) group, generation of tumor mass was delayed so that it was found from the 24th day in the PPD-HAMP group, and thus tumor mass generation-suppressing effect was observed for this group. However, ratios of the mice remained to be tumor-free on the 50th day from the challenge and thereafter in the both groups were the same, 6/10 (60%). On the other hand, generation of tumor mass was not observed at all (8/8 or 100%) in the mGM-CSF-hIL-2-PPD-HAMP administration group, and as a result of a test for difference of the population rate (chi square test) performed between the 2 groups, this group and the control group, the two-sided p value was 0.0425, and there was a statistically significant difference.

On the basis of combination of these results and the results of Example 10 shown in FIG. 12, it is considered that PPD-HAMP (whether it is added with nega-TuMP or not) has an immunoadjuvant activity that can suppress exacerbation of tumor, and when a cytokine, mGM-CSF or hIL-2, adsorbed on nega-TuMP is further added to it, stronger and more effective immunoadjuvant activity is exhibited.

It is widely known to those skilled in the art that antigenicity of tumor antigen contained in naturally occurring tumor cells is generally low, and it cannot easily induce antitumor immunoreactions in the living body (therefore, tumor is generated). Therefore, it is obvious for those skilled in the art that if a substance that shows a high antigenicity (for example, antigen derived from exogenous organism such as virus) is used instead of the tumor antigen used above (LLC cell lysate), it can be a vaccine that can oppose to the infectious disorder caused by that virus, because the mechanism of immunoreactions is the same irrespective of type of antigen. Further, if an immunostimulant containing PPD-HAMP added with mGM-CSF-MP or IL-2-MP is used as an immunoadjuvant, effective antitumor immunoreactions can be induced even for such tumor antigens showing low antigenicity as mentioned above. Therefore, it is also obvious for those skilled in the art that, even with another disease factor substance derived from the inside of the body and showing low antigenicity, a composition using the substance as the antigen and serving as a vaccine for a treatment of the corresponding disease can also be prepared.

INDUSTRIAL APPLICABILITY

The complex of the present invention has an immunostimulating action, and can effectively stimulate antigen-presenting cells, and accordingly, the complex is useful as an immunostimulant for therapeutic treatment of a disease such as tumor, as well as prophylactic treatment of postoperative recurrence or metastasis of a malignant tumor.

What is claimed is:

1. A complex comprising a carrier containing a protein obtained from serum or a protein obtained from plasma solidified by denaturation coagulation, and a protein having a peroxidase-like activity and carried by the carrier.

2. The complex according to claim 1, wherein the protein having a peroxidase-like activity is carried in an undenatured state or a denatured state.

3. The complex according to claim 1, wherein the protein having a peroxidase-like activity is carried in a state that it is solidified by denaturation coagulation together with the protein obtained from serum or the protein obtained from plasma.

4. The complex according to claim 1, wherein the protein having a peroxidase-like activity is hemoglobin or myoglobin.

5. The complex according to claim 1, which further carries one kind or two or more kinds of immunostimulating substances.

6. The complex according to claim 5, wherein the immunostimulating substance consists of one kind or two or more kinds of substances selected from the group consisting of a purified tuberculin, a BCG bacteria extract, a cytokine, a Toll-like receptor ligand, a NOD-like receptor agonist, a RIG-like receptor agonist, a C type lectin receptor agonist, an exogenous DNA that binds with a cyclic GMP-AMP synthase, an alarmin, an antigen, and an antibody.

7. An immunostimulant containing the complex according to claim 1, wherein the immunostimulant further comprises one or more immunostimulating substance(s) or an immunoreaction-suppressing action substance.

8. An immunostimulating composition containing the immunostimulant according to claim 7, and albumin-heparin coacervate precipitates.

9. The immunostimulating composition according to claim 8, wherein the albumin-heparin coacervate precipitates are albumin heparin coacervate precipitates adsorbed with a cytokine.

10. The immunostimulating composition according to claim 9, wherein the cytokine consists of one kind or two or more kinds of substances selected from the group consisting of granulocyte-macrophage colony-stimulating factor, interleukin-2, and interferon γ.

11. A medicament comprising a combination of the immunostimulant according to claim 7, and an immunoreaction-suppressing action inhibitor.

12. The medicament according to claim 11, wherein the immunoreaction-suppressing action inhibitor is an immune checkpoint inhibitor.

13. The medicament according to claim 12, wherein the immune checkpoint inhibitor consists of one kind or two or more kinds of antibodies selected from the group consisting of an anti-PD-1 antibody, an anti-PD-L1 antibody, an anti-PD-L2 antibody, an anti-CTLA-4 antibody, an anti-CD40 antibody, an anti-CD137 antibody, an anti-OX40 antibody, an anti-TGF-β antibody, an anti-LAG3 antibody, an anti-B7-H3 antibody, an anti-B7-H4 antibody, an anti-TIM3 antibody, an anti-CD96 antibody, and an anti-TIGIT antibody.

14. A vaccine comprising a combination of the immunostimulant according to claim 7, and a tumor antigen, wherein the tumor antigen is derived from a lung cancer cell.

15. The vaccine according to claim 14, which is configured for use in therapeutic treatment of a malignant tumor and/or prophylactic treatment of recurrence or metastasis of a malignant tumor.

* * * * *